(12) United States Patent
Udugamasooriya et al.

(10) Patent No.: US 11,865,157 B2
(45) Date of Patent: Jan. 9, 2024

(54) COMPOSITIONS AND METHODS OF TARGETING CANCER STEM CELLS

(71) Applicants: University of Houston System, Houston, TX (US); The Board of Regents of the University of Texas System, Austin, TX (US)

(72) Inventors: Damith Gomika Udugamasooriya, Katy, TX (US); Aaron Raymond, Houston, TX (US); John Minna, Dallas, TX (US)

(73) Assignees: University of Houston System, Houston, TX (US); The Board of Regents of the University of Texas System, Austin, TX (US)

( * ) Notice: Subject to any disclaimer, the term of this patent is extended or adjusted under 35 U.S.C. 154(b) by 0 days.

(21) Appl. No.: 18/157,648

(22) Filed: Jan. 20, 2023

(65) Prior Publication Data

US 2023/0218708 A1    Jul. 13, 2023

Related U.S. Application Data

(62) Division of application No. 16/334,528, filed as application No. PCT/US2017/052184 on Sep. 19, 2017, now Pat. No. 11,660,325.

(60) Provisional application No. 62/396,274, filed on Sep. 19, 2016.

(51) Int. Cl.
| | | |
|---|---|---|
| A61K 38/08 | (2019.01) | |
| C07K 7/06 | (2006.01) | |
| A61K 47/65 | (2017.01) | |
| A61K 47/64 | (2017.01) | |
| A61P 35/00 | (2006.01) | |

(52) U.S. Cl.
CPC .............. *A61K 38/08* (2013.01); *A61K 47/64* (2017.08); *A61K 47/65* (2017.08); *A61P 35/00* (2018.01); *C07K 7/06* (2013.01)

(58) Field of Classification Search
CPC .................................. C07K 7/06; A61K 38/08
See application file for complete search history.

(56) References Cited

U.S. PATENT DOCUMENTS

| | | |
|---|---|---|
| 2005/0118645 A1 | 6/2005 | Michelitsch et al. |
| 2008/0187938 A1 | 8/2008 | Wicha et al. |
| 2015/0030615 A1 | 1/2015 | Derr et al. |
| 2015/0105328 A1 | 4/2015 | McLaughlin et al. |

FOREIGN PATENT DOCUMENTS

| | | |
|---|---|---|
| WO | WO 2008-013966 | 1/2008 |
| WO | WO 2008-036419 | 3/2008 |

OTHER PUBLICATIONS

Bhowmik et al., "Design, synthesis and use of peptoids in the diagnosis and treatment of cancer", Frontiers in Bioscience, Elite, 2017, 106, pp. 1-4.
Boohaker et al., "The Use of Therapeutic Peptides to Target and to Kill Cancer Cells", Curr Med Chem. 2012: 19(22):3794-3804.
Hooks, et al., "Development of homomultimers and heteromultimers of lung cancer-specific peptoids." *Peptide Science* 96.5 (2011): 567-577.
International Preliminary Report on Patentability issued in International Application No. PCT/US2017/052184, dated Mar. 19, 2019.
International Search Report and Written Opinion issued in International Application No. PCT/US2017/052184, dated Jan. 23, 2018.
Kwon et al., "Application of Proteomics in Cancer: Recent Trends and Approaches for Biomarkers Discovery", Frontiers in Medicine, 2021, pp. 1-18.
Matharage, et al., "Unbiased Selection of Peptide-Peptoid Hybrids Specific for Lung Cancer Compared to Normal Lung Epithelial Cells." *ACS0 Chemical Biology* 10.12 (2015): 2891-2899.
Walcher et al., "Cancer Stem Cells—Origins and Biomarkers: Perspectives for Targets Personalized Therapies", Frontiers in Immunology, Aug. 2020, pp. 1-33.
Singh, et al. "Identification of the minimum pharmacophore of lipid-phosphatidylserine (PS) binding peptide-peptoid hybrid PPS1D1." *Bioorganic & Medicinal Chemistry* 24.18 (2016): 4470-4477.
Bhowmik et al., "Design, synthesis and use of peptoids in the diagnosis and treatment of cancer", *Frontiers in Bioscience*, Elite, 2017, pp. 1-4-106.
International Preliminary Report on Patentability issued in International Application Np. PCT/US2017/052184, dated Mar. 19, 2019.

*Primary Examiner* — Lianko G Garyu
(74) *Attorney, Agent, or Firm* — Parker Highlander PLLC

(57) ABSTRACT

Described herein are pharmaceutical compositions containing peptoids of general formula (I), (II), or (III) capable of reducing proliferation of cancer stem cells in a subject and methods of treatment or prophylactic administration of these pharmaceutical compositions to treat cancer. Also provided herein are method of detecting and treating cancerous cell masses by use of peptoids of general formula (I), (II), or (III).

11 Claims, 30 Drawing Sheets

(A)

(B)

Fig. 2. (A) Peptide vs Peptoid
(B) Peptoid Synthesis outline

PCS1  PCS2

PCS3

PCS1D1  PCS2D1

| | Pre-Sx Fentagel | Pre-Sx Magnetic Bead | Post Magnetic Bead | Post Magnetic Bead |
|---|---|---|---|---|
| HDEC-0151 | - | - | ND | ND |
| HDEC-871 | - | - | ND | ND |
| TT1835 | - | - | ND | ND |
| TT1895 | - | + | ND | ND |
| TT1810 | - | - | ND | - |
| TT1883 | + | +++ | ND | ND |
| TT353 | ++ | +++ | + | + |
| TT2127 | ++ | +++ | - | - |
| TT1893 | ++++ | ++++ | - | - |
| TT1809 | ++++ | ++++ | - | - |
| TT356 | +++++ | +++++ | - | - |
| TT489 | +++++ | +++++ | ++ | - |
| HCC-4017 | +++++ | +++++ | + | ++ |
| TT2078 | +++++ | +++++ | - | + |
| HCC-982 | +++++ | +++++ | - | + |
| TT481 | ND | - | + | ND |
| HCC-960 | ND | +++ | + | ND |
| TT1875 | ND | +++++ | - | - |
| TT1929 | ND | +++++ | - | - |

WCL: whole cell lysate

| Relative binding % | | | |
| --- | --- | --- | --- |
| Cell line | PCS1 | PCS2 | PC3 |
| HBEC3KT | - | - | - |
| H2009 | - | ++++ | - |
| HCC4017 | ++ | +++++ | ++ |
| H460 | ++ | +++++ | - |
| H1975 | - | +++++ | - |
| H2122 | - | +++ | - |
| H2073 | - | +++++ | ++ |
| H1993 | - | +++ | - |
| H1299 | - | +++++ | - |
| H1155 | - | - | ++ |
| H1395 | ++ | + | |
| H358 | + | +++ | + |
| H1693 | - | ++++ | - |

*Sullivan et al. Cancer Res. 2010
ND= No Data; - = 0-1%; += 2-10%;
++ = 11-20%; +++ = 20-30%;
++++ = 31-40%; +++++ = >40%

FIG. 20

COMPOSITIONS AND METHODS OF TARGETING CANCER STEM CELLS

REFERENCE TO RELATED APPLICATION

This application is a divisional of application Ser. No. 16/334,528 filed Mar. 19, 2019 which is a § 371 National Stage Application of International Application No. PCT/US2017/052184, filed on Sep. 19, 2017, which claims the benefit of U.S. Provisional Application No. 62/396,274, filed on Sep. 19, 2016, which is incorporated herein by reference in its entirety their entireties.

GOVERNMENT SUPPORT

This invention was made with government support under grant number CA070907 awarded by the National Institutes of Health. The government has certain rights in the invention.

FIELD OF INVENTION

The present disclosure relates to certain compounds that target cancer stem cells, and more specifically to certain peptidomimetic compounds that selectively target cancer stem cells.

BACKGROUND

Despite significant advances in targeting cancer and in understanding its molecular mechanisms, many cancer drug-leads fail during or before clinical trials. Moreover, the efficacy of cancer therapeutics currently in clinical use is limited by the rapid development of drug resistance. Many cancer therapeutics are designed on the basis that cancer consists of a homogenous group of rapidly growing cells. However, it is increasingly recognized that cancer consists of heterogeneous cell populations; this heterogeneity is partially responsible for resistance to cancer therapeutics.

In a cancer stem cell model of cancer progression, the cancer stem cells (CSC) are a small subset of cells with stem cell-like traits within a heterogeneous tumor, and have tumorigenic and invasive potential. These cells are also called tumor initiating cells. CSCs can self-renew, differentiate to generate other cancer cell types in a tumor, and can form tumors in isolation. CSCs persist following conventional treatment, and then proliferate to drive tumor reformation, leading to relapse. By contrast, treatments that specifically target CSCs would leave only non-tumorigenic cells behind, which cannot rapidly expand, can easily be targeted by conventional treatments and thereby greatly reducing the risk of future relapses or metastases. The CSC model helps to explain the outcomes seen with some traditional cancer therapies such as chemotherapy, radiation, and surgery. While these therapies can successfully remove an initial tumor mass, if they do not also eliminate persisting CSCs, a significant risk of relapse remains. Thus, the development of therapeutics that specifically target CSCs is of vital importance for reducing this risk and for improving patient outcomes. CSC biology is currently poorly understood; as a result, conventional drug development approaches that rely on prior knowledge of biomarkers to target cells are not readily applicable to developing compounds that specifically target CSCs. CSC-based therapeutic and diagnostic strategies face many challenges due to paucity of true known CSC biomarkers and proper CSC drug-lead identification tools.

Peptoids (oligo-N-substituted glycines) closely resemble peptides except that their side chains extend from the main chain nitrogen rather than from the a-carbon. These oligomers are achiral, protease resistant and highly cell permeable. Peptoid synthesis is straightforward. To add one residue (equivalent to an amino acid of a peptide) requires only two chemical steps and each of these can be completed by two, 15-second microwave pulses. Bromoacetic acid coupling brings the 2-carbon unit. The bromine can be replaced by any amine group, which dramatically expands the repertoire of chemical space. Large combinatorial libraries of peptoids (in the millions) are synthesized easily, inexpensively, and rapidly (within 2-3 days). Peptoid sequences are deduced with high sensitivity by Edman degradation or by mass spectrometry. Peptoids are rich sources of protein-binding ligands that can antagonize receptors and intracellular protein molecules. Many antimicrobial peptoids have also been reported. Peptoids are also non-immunogenic in mice. Taken together, peptoids can be considered as excellent alternatives for drug development to the expensive conventional molecular drug classes, such as small organics, antibodies, and peptides.

SUMMARY

Disclosed herein are compounds and methods addressing the shortcomings of the art, and may provide any number of additional or alternative advantages. Described herein are compounds, compositions and methods for targeting CSCs, reducing or even preventing the proliferation of CSCs, reducing the colony forming potential of cancerous cell masses. Embodiments described herein include a pharmaceutical composition for reducing proliferation of cancer stem cells and having the general formula (I), an isomer thereof, or a pharmaceutically acceptable derivative thereof:

General formula (I)

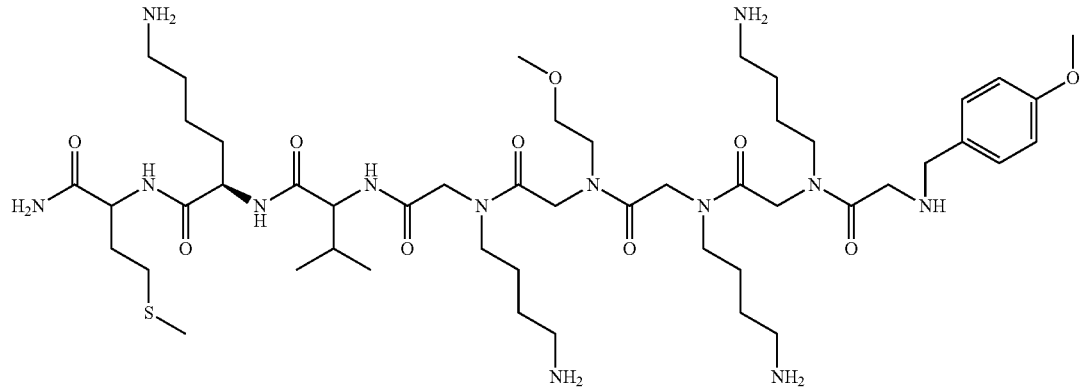

Other embodiments include pharmaceutical compositions that include a therapeutically effective amount of a pharmaceutical composition having the general formula (I), and a pharmaceutically acceptable carrier. Certain embodiments include methods for reducing proliferation of cancer stem cells in a subject by administering to the subject a therapeutically effective amount of a pharmaceutical composition having the general formula (I). The cancer stem cells can be present as part of a cancerous cell mass. In certain embodiments, the cancerous cell mass contains cells selected from the group consisting of leukemia, glioblastoma, melanoma, colon cancer, prostate cancer, lung cancer, pancreatic cancer, hepatic cancer, ovarian cancer, and breast cancer. Provided herein are methods of detecting presence of cancer stem cells in a human tissue sample. The method includes the analyzing the human tissue sample for a specific interaction with a peptoid having the general formula (I), the specific interaction being indicative of presence of cancer stem cells.

Embodiments described herein include a pharmaceutical composition for reducing proliferation of cancer stem cells and having the general formula (II), an isomer thereof, or a pharmaceutically acceptable derivative thereof.

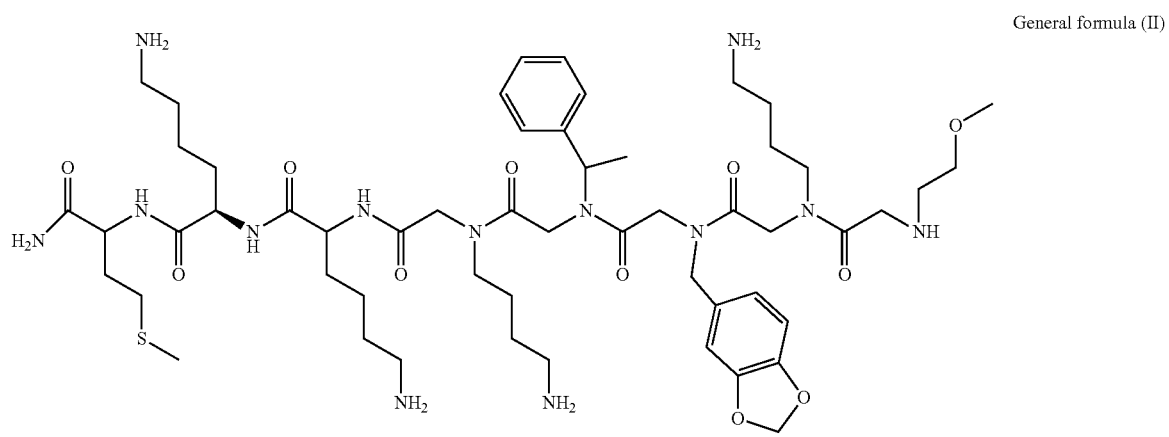

General formula (II)

Other embodiments include pharmaceutical compositions that include a therapeutically effective amount of a pharmaceutical composition having the general formula (II), and a pharmaceutically acceptable carrier. Certain embodiments include methods for reducing proliferation of cancer stem cells in a subject by administering to the subject a therapeutically effective amount of a pharmaceutical composition having the general formula (II). The cancer stem cells can be present as part of a cancerous cell mass. In certain embodiments, the cancerous cell mass contains cells selected from the group consisting of leukemia, glioblastoma, melanoma, colon cancer, prostate cancer, lung cancer, pancreatic cancer, hepatic cancer, ovarian cancer, and breast cancer. Provided herein are methods of detecting presence of cancer stem cells in a human tissue sample. The method includes the analyzing the human tissue sample for a specific interaction with a peptoid having the general formula (II), the specific interaction being indicative of presence of cancer stem cells. The specific interaction can be mediated by one or more biomarkers, such as plectin present in cancer stem cells. The cancer stem cells can be present as part of a cancerous cell mass. In certain embodiments, the cancerous cell mass contains cells selected from the group consisting of leukemia, glioblastoma, melanoma, colon cancer, prostate cancer, lung cancer, pancreatic cancer, hepatic cancer, ovarian cancer, and breast cancer.

Embodiments described herein include a pharmaceutical composition for reducing proliferation of cancer stem cells and having the general formula (III), an isomer thereof, or a pharmaceutically acceptable derivative thereof.

General formula (III)

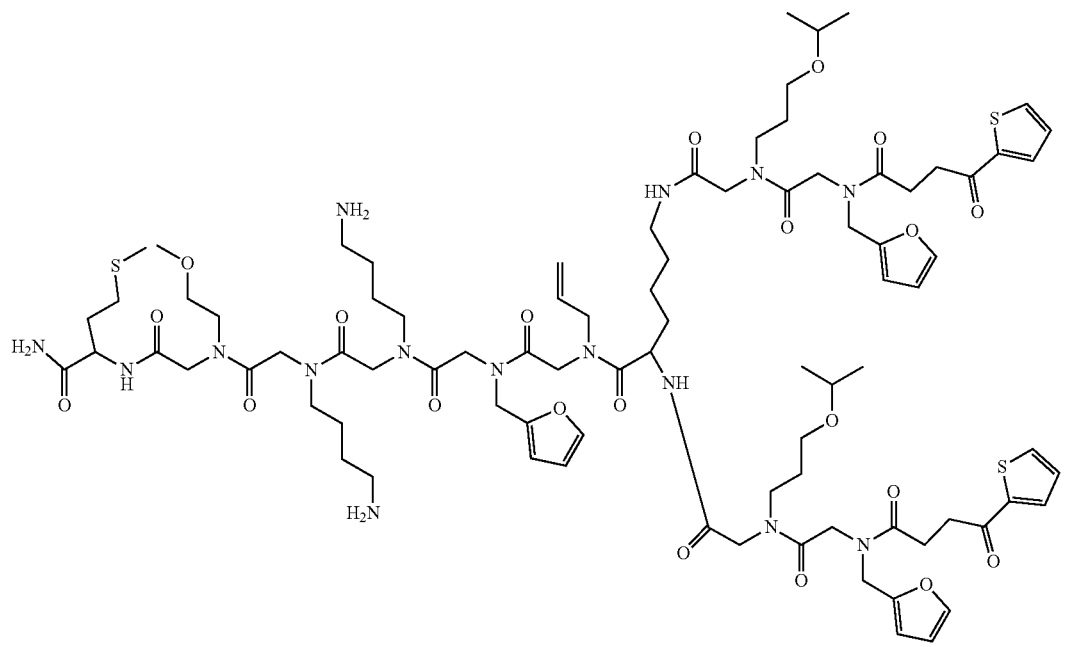

Other embodiments include pharmaceutical compositions that include a therapeutically effective amount of a pharmaceutical composition having the general formula (III), and a pharmaceutically acceptable carrier. Certain embodiments include methods for reducing proliferation of cancer stem cells in a subject by administering to the subject a therapeutically effective amount of a pharmaceutical composition having the general formula (III). The cancer stem cells can be present as part of a cancerous cell mass that contains cells selected from the group consisting of leukemia, glioblastoma, melanoma, colon cancer, prostate cancer, lung cancer, pancreatic cancer, hepatic cancer, ovarian cancer, and breast cancer. Provided herein are methods of detecting presence of cancer stem cells in a human tissue sample. The method includes the analyzing the human tissue sample for a specific interaction with a peptoid having the general formula (III), the specific interaction being indicative of presence of cancer stem cells. The specific interaction can be mediated by one or more biomarkers present in cancer stem cells.

Numerous other aspects, features and benefits of the present disclosure may be made apparent from the following detailed description taken together with the drawing figures. The pharmaceutical compositions can include compounds described herein, other components, or ingredients depending on desired prevention and treatment goals. It should be further understood that both the foregoing general description and the following detailed description are exemplary and explanatory and are intended to provide further explanation of the invention as claimed.

BRIEF DESCRIPTION OF THE DRAWINGS

The present disclosure can be better understood by referring to the following figures. The components in the figures are not necessarily to scale. The emphasis is instead placed upon illustrating the principles of the disclosure. In the figures, reference numerals designate corresponding parts throughout the different views.

FIG. 5A show chemical structures of the compounds PCS1, PCS2, PCS3, PCS1D1, and PCS2D1, and FIG. 5B shows the extended dimer series PCS2D2.1, PCS2D2.2, PCS2D2.3, PCS2D2.4, and PCS2D2.5 compounds with various linker lengths

FIG. 9 is a tabular representation of the relative binding affinity of lung cancer cell lines to the PCS1, PCS2, and PCS3-carrying beads.

FIG. 20 is a tabular representation of the relative binding affinity of lung cancer cell lines to the PCS1, PCS2, and PCS3-carrying beads.

DETAILED DESCRIPTION

Figure 1:
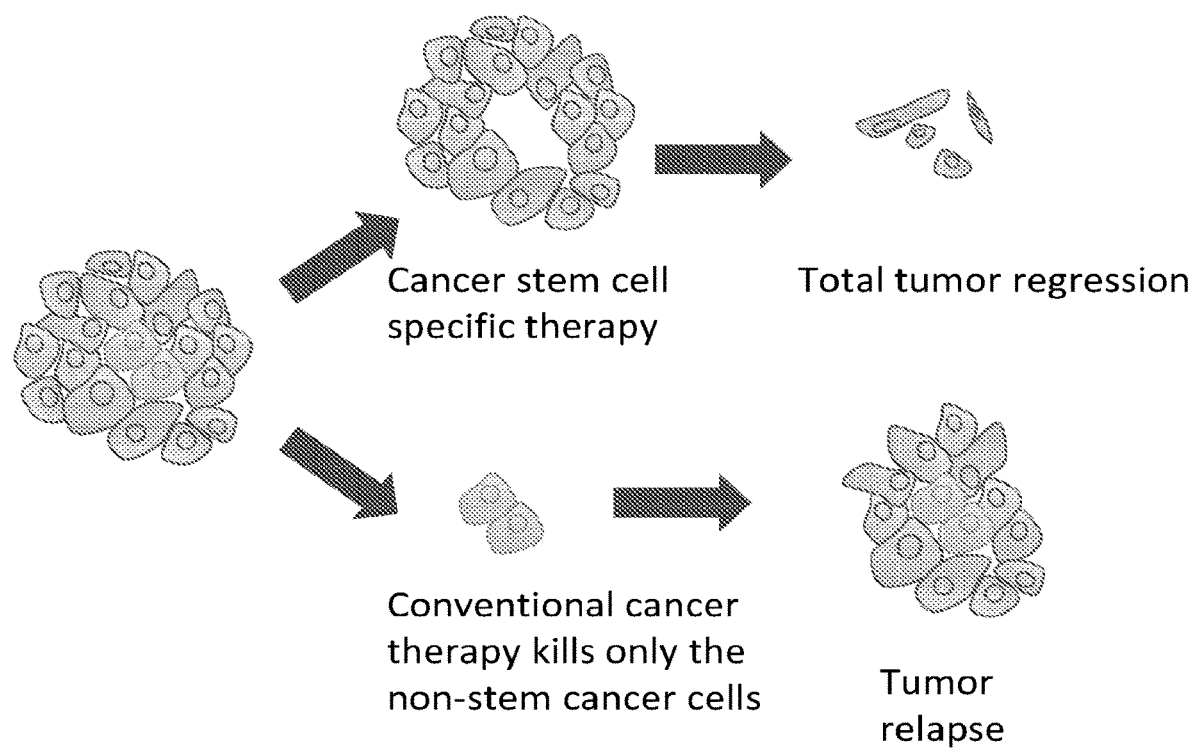
FIG. 1 is an illustration of the difference between traditional Cancer therapies and CSC-targeted therapies, according to an exemplary embodiment.
Figure 2A:
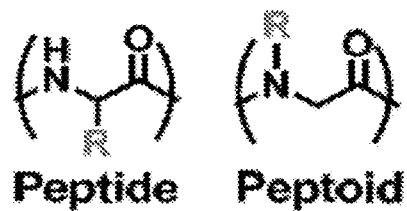
FIG. 2A is an illustration of the difference in the bonds between a peptide and a peptoid.
Figure 2B:
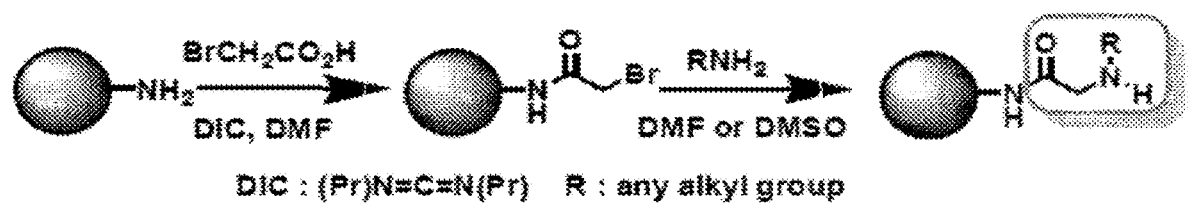
FIG. 2B is an illustration of the peptoid synthesis reaction.

Reference will now be made to the exemplary embodiments illustrated in the drawings, and specific language will be used here to describe the same. It will nevertheless be understood that no limitation of the scope of the invention is thereby intended. Alterations and further modifications of the inventive features illustrated here, and additional applications of the principles of the inventions as illustrated here, which would occur to one skilled in the relevant art and having possession of this disclosure, are to be considered within the scope of the invention.

Embodiments described herein include a pharmaceutical composition for reducing proliferation of cancer stem cells and having the general formula (I) or (II) or (III), an isomer thereof, dimers thereof, or a pharmaceutically acceptable derivative thereof.

General formula (I)

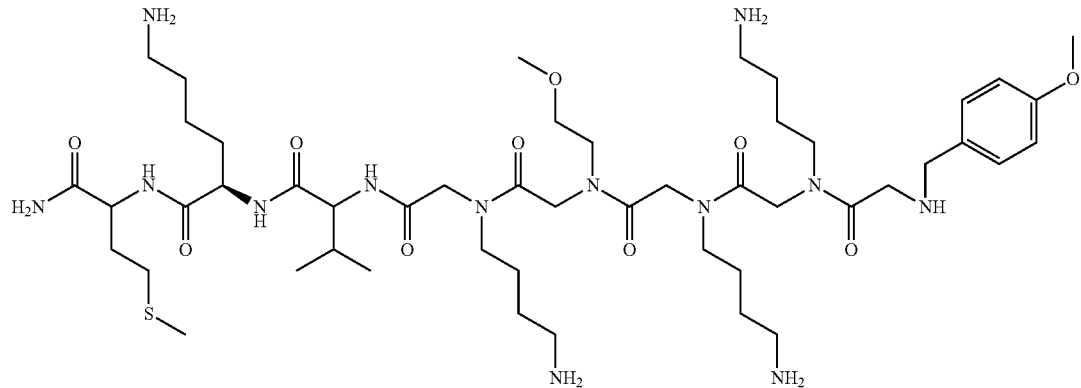

General formula (II)

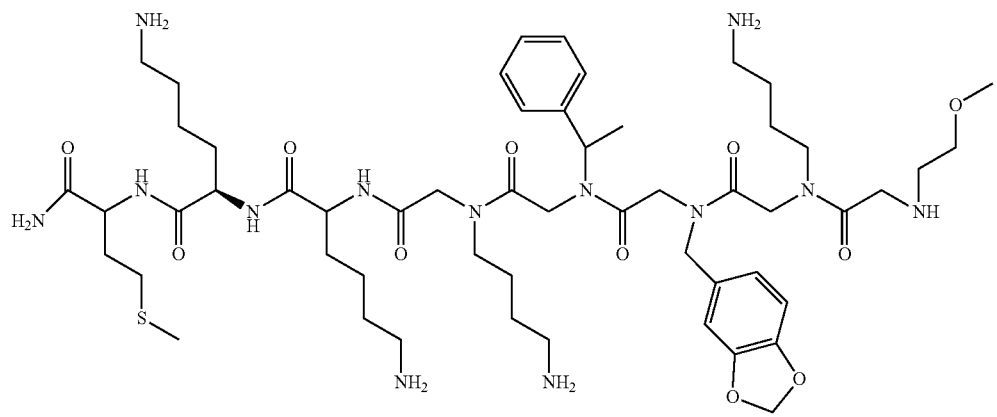

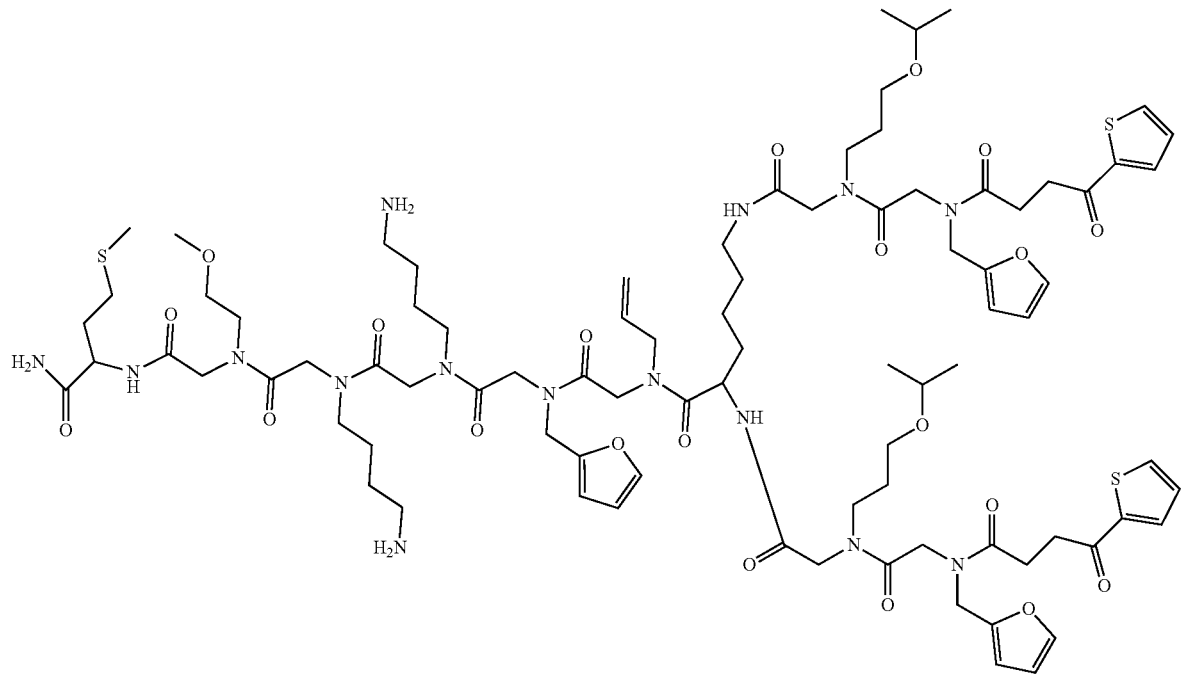

General formula (III)

Other embodiments include pharmaceutical compositions that include a therapeutically effective amount of a pharmaceutical composition having the general formula (I) or (II) or (III), and a pharmaceutically acceptable carrier. Certain embodiments include methods for reducing proliferation of cancer stem cells in a subject by administering to the subject a therapeutically effective amount of a pharmaceutical composition having the general formula (I) or (II) or (III). The cancer stem cells can be present as part of a cancerous cell mass. In certain embodiments, the cancerous cell mass contains cells selected from the group consisting of leukemia, glioblastoma, melanoma, colon cancer, prostate cancer, lung cancer, pancreatic cancer, ovarian cancer and breast cancer. The pharmaceutical compositions having the general formula (I) or (II) or (III) can be used individually or in combination with each other or in combination with an effective amount of a chemotherapeutic agent As used here, the following terms may have the following definitions:

A "pharmaceutical composition" refers to a mixture of one or more of the peptoids described herein, or a pharmaceutically acceptable salt, solvate, hydrate or prodrug thereof as an active ingredient, and at least one pharmaceutically acceptable carrier or excipient. The purpose of a pharmaceutical composition is to facilitate administration of a peptoid to a subject. In another aspect, the invention provides a pharmaceutical composition including a peptoid of one of the formulae described herein, or a pharmaceutically acceptable salt thereof, and a pharmaceutically acceptable carrier or excipient. In some embodiments, the pharmaceutical composition includes two or more pharmaceutically acceptable carriers and/or excipients.

The term "pharmaceutically acceptable derivative" as used herein refers to and includes any pharmaceutically acceptable salt, pro-drug, metabolite, ester, ether, hydrate, polymorph, solvate, complex, and adduct of a peptoid described herein which, upon administration to a subject, is capable of providing (directly or indirectly) the active ingredient. For example, the term "a pharmaceutically acceptable derivative thereof" of peptoids of general formula (I), (II), or (III) includes all derivatives of the peptoids of general formula (I), (II), or (III) (such as salts, pro-drugs, metabolites, esters, ethers, hydrates, polymorphs, solvates, complexes, and adducts) which, upon administration to a subject, are capable of providing (directly or indirectly) the peptoids of general formula (I), (II), or (III).

As used herein, the term "pharmaceutically acceptable salt" refers to those salts, which retain the biological effectiveness and properties of the parent peptoid. Moreover, unless otherwise indicated, a pharmaceutically acceptable salt includes salts of acidic or basic groups, which may be present in the peptoids of the formulae disclosed herein. The present invention also relates to a process for the preparation of the above pharmaceutically acceptable salts, their derivatives, their analogs, their tautomeric forms, their stereoisomers, their polymorphs, and pharmaceutical compositions containing them.

Certain embodiments relate to pharmaceutically acceptable salts formed by the peptoids of general formula (I), (II), or (III), their derivatives, their analogs, their tautomeric forms, their stereoisomers, their polymorphs and pharmaceutically acceptable compositions containing them.

Embodiments of the invention include pharmaceutical compositions including peptoids of general formula (I), (II), or (III), or a pharmaceutically acceptable salt thereof, and a pharmaceutically acceptable carrier or excipient. Pharmaceutically acceptable ingredients, such as excipients, diluents, fillers, binders, and carriers can be inert or actively contribute to the delivery and distribution of the peptoids of general formula (I), (II), or (III). The formulations used in embodiments herein include excipients, such as microcrystalline cellulose, lactose monohydrate, hydroxypropyl cellulose, croscarmellose sodium and magnesium stearate, preferably at least about 50 wt %, such as in the range from about 50% to about 95 wt %, including the range from about 50-90 wt %, and more preferably in the range from about 55-85 wt %, such as in the range from about 60% to about 85 wt %, or in the range from about 65 wt % to about 80 wt %, including about 60 wt %, about 65 wt %, about 70 wt %, about 75 wt %, or about 80 wt %.

As used herein, unless otherwise noted, the terms "treating", "treatment" and the like, shall include the management and care of a subject or patient (preferably mammal, more preferably human) for the purpose of combating a disease, condition, or disorder and includes the administration of a peptoid of the present invention to prevent the onset of the symptoms or complications, alleviate the symptoms or complications, or eliminate the disease, condition, or disorder. The term "therapeutically effective amount" as used herein, means that amount of active peptoid or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, "cancer" refers to all types of cancers or neoplastic growth or tumors found in mammals, including but not limited to leukemia, glioblastoma, melanoma, colon cancer, prostate cancer, lung cancer, pancreatic cancer, hepatic cancer, ovarian cancer, and breast cancer. Other examples include hepatocellular carcinoma, colorectal adenocarcinoma, kidney cancer, thyroid cancer, neuroblastoma, sarcoma, cervical cancer, endometrial carcinoma, malignant seminoma, esophageal cancer, and head and neck cancer.

The compositions herein are formulated in accordance to the mode of potential administration. Thus, if the composition is intended to be administered intranasally or by inhalation, for example, the composition may be a converted to a powder or aerosol form, as conventional in the art, for such purposes. Other formulations, such as for oral or parenteral delivery, are also used as conventional in the art. Compositions for administration herein may form solutions, suspensions, tablets, pills, capsules, sustained release formulations or powders.

An "effective amount" is an amount that will bring about the desired response in a subject, such as reduction in symptoms, prevention of infection, and elimination of existing viral infection in a subject. Illustratively, an effective amount of the compositions of this invention ranges from nanogram/kg to milligram/kg amounts for young children and adults. Equivalent dosages for lighter or heavier body weights can readily be determined. The dose should be adjusted to suit the individual to whom the composition is administered and will vary with age, weight and metabolism of the individual. The exact amount of the composition required will vary from subject to subject, depending on the species, age, weight and general condition of the subject, the particular peptide or polypeptide used, its mode of administration and the like. An appropriate amount can be determined by one of ordinary skill in the art using only routine experimentation given the teachings herein. One skilled in the art will realize that dosages are best optimized by the practicing physician or veterinarian and methods for determining dose amounts and regimens and preparing dosage forms are described, for example, in Remington: The Science and Practice of Pharmacy, 22nd edition.

PCS1, PCS2 and PCS3 are novel peptoid compounds that specifically recognize and antagonize CSCs over the remaining cancer cells from the same tumor. These are the first peptoids developed targeting CSCs. Currently there are very few methods to isolate and identify/diagnose CSCs from a tumor, blood circulation and/or cancer cell culture sample, and those are not always accurate or reliable. Each of these peptoids has the capacity to be developed into a novel identification and sorting method for a CSC-subpopulation in tumors. There are no reliable antagonists or drugs available for CSC targeting. Each one of these peptoid drug leads can be developed into CSC-directed therapeutics, which could have a considerable impact on patient survival. These peptoids will bind to biomarkers specific for CSCs. Provided herein are methods of detecting presence of cancer stem cells in a human tissue sample. The method includes the analyzing the human tissue sample for a specific interaction with PCS1, PCS2 or PCS3, the specific interaction being indicative of presence of cancer stem cells. The specific interaction can be mediated by one or more biomarkers, such as plectin present in cancer stem cells. The cancer stem cells can be present as part of a cancerous cell mass. In certain embodiments, the cancerous cell mass that contains cells selected from the group consisting of leukemia, glioblastoma, melanoma, colon cancer, prostate cancer, lung cancer, pancreatic cancer, hepatic cancer, ovarian cancer, and breast cancer. The identification of CSC specific biomarkers such as plectin will facilitate development of diagnostics and therapeutics. The main drug classes currently used in the clinic, such as small organic molecules, peptides and antibodies, carry their own weaknesses and problems, more in terms of biocompatibilities as well as costs or production. In contrast, the advantageous properties of these peptoids, such as their high serum stability, cell permeability, non-immunogenicity, and their simple and cost-effective synthesis make them highly promising candidates for development of diagnostics and therapeutics. Optimal dosages of the peptoids to be administered may be readily determined by those skilled in the art, and will vary with the particular compound used, the mode of administration, the strength of the preparation, the mode of administration, the number of consecutive administrations within a limited period and the advancement of the disease condition. In addition, factors associated with the particular patient being treated, including patient age, weight, diet and time of administration, will result in the need to adjust dosages. The term "subject" as used herein, refers to an animal, preferably a mammal, most preferably a human, who has been the object of treatment, observation or experiment. Preferably, the subject has experienced and/or exhibited at least one symptom of the disease or disorder to be treated and/or prevented.

One of the biomarkers identified as present in CSC and targeted by PCS2 is the structural protein, plectin, that is found in cell cytosol and belongs to a family of proteins important in maintaining cell shape and tissue integrity. In epithelial cells, plectin functions as a molecular adherent and connects cytokeratins and certain integrins. Plectin has been reported to exhibit functions affecting cellular signals and responsive activities mediated by stress, cellular migration, polarization as well as the dynamic movement of actin filaments. Results from the use of peptoid PCS2 indicate a role of plectin in CSC structure and/or function, and so blocking this protein using compositions disclosed herein may reduce the presence of CSCs in a cancerous mass; and thus improving susceptibility of the cancerous mass to conventional treatment and preventing metastasis.

To provide a more concise description, some of the quantitative expressions herein are recited as a range from about amount X to about amount Y. It is understood that wherein a range is recited, the range is not limited to the recited upper and lower bounds, but rather includes the full range from about amount X through about amount Y, or any amount or range therein.

To provide a more concise description, some of the quantitative expressions given herein are not qualified with the term "about". It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

EXAMPLES

The following Examples are set forth to aid in the understanding the invention, and are not intended and should not be construed to limit in any way the invention set forth in the claims, which follow thereafter.

Example 1

Figures 3A, 3B, 3C:
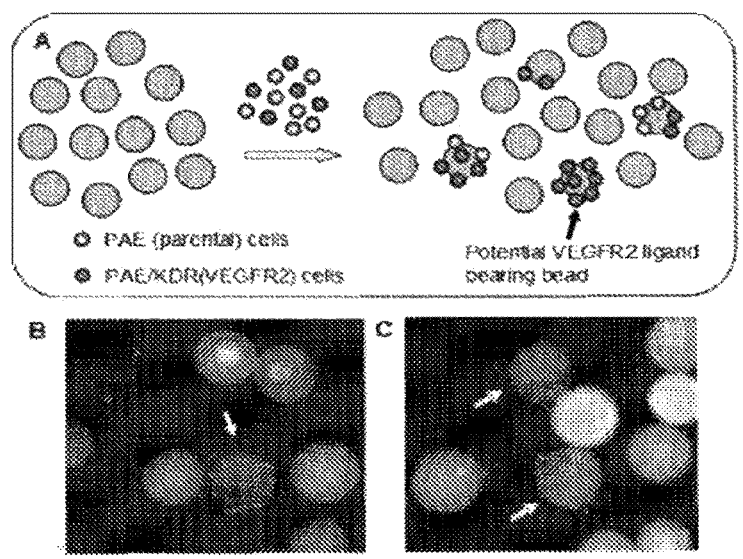
FIG. 3A is an illustration of the on-bead two-color cell screening assay.
FIG. 3B is a microscopic view of beads bound only by red-colored cells, which have the specific targets, e.g. VEGFR2, according to an exemplary embodiment.
FIG. 3C is a microscopic view of beads bound by both red-colored and green-colored cells, both of which have the non-specific targets, according to an exemplary embodiment.

Highly Specific Lead Peptoids Identified Using on-Bead Two-Color (OBTC) Combinatorial Cell Screen A unique unbiased selection approach was performed that identified candidates that target cell surface biomolecules predominantly found on CSCs but not present on remaining cancer cells. Candidates were from a class of biologically manipulatable and cost effective peptidomimetics, called peptoids. A combinatorial library of peptoid compounds were developed for the purpose of cancer drug development. Peptoids closely resemble peptides, except the side chain extends from the Nitrogen. Peptoids are serum stable, non-immunogenic, cell permeable, and easy to synthesize. The on-bead two-color (OBTC) combinatorial cell cell-screening technology was developed to directly isolate highly specific ligands for cell-surface receptors, as shown in FIG. 3. In this assay, two identical cell groups, which differ only by the presence (red stained) or absence (green stained) of a particular receptor, are exposed to one-bead one-compound peptoid library beads. Each bead carries a unique peptoid sequence with many copies (FIG. 3A). If a bead is bound only by the red stained, receptor-overexpressing cells (FIG. 3B), the peptoid on this bead binds only to this overexpressed receptor and not to other cell-surface molecules. If the peptoid on the bead binds to any other cell-surface molecule, it will be bound by green cells too and that can instantly be disregarded (FIG. 3C). This assay was previously used to identify highly specific antagonist peptoids for VEGFR2, T-cell receptors, Fibulin-5, and lipid-phosphatidylserine (PS). The uniqueness of the OBTC assay is its ability to recognize differences between two cell surfaces, which allows its application in a uniquely unbiased fashion. For example, in an earlier study, HCC4017 lung cancer cells were stained in red and HBEC30KT normal cells from the same patient in green, mixed the cells 1:1 and exposed to the library beads. Only red cell-bound beads were isolated to identify a peptoid that binds to a biomolecule present specifically on cancer cell surface but not on normal cells. One of the identified peptoids bound strongly to and killed HCC4017 cancer cells, both in vitro and vivo, but did not affect normal cells. The target of the peptoid was identified as lipid-PS, which is found only on the surface of cancer cells.

To identify potential CSC-targeting peptoids, this OBTC assay was used to target CSCs over the remaining non-CSC cancer cells derived from same cell line, by using the similar unbiased approach described in the previous paragraph. CSCs that were sorted out from H358 lung cancer cells in the presence of the remaining non-CSC H358 cells were targeted. The H358 cells were sorted by the commercially available ALDEfluor assay kit, which is based on activity of known CSC biomarker—aldehyde dehydrogenase (ALDH). The ALDH$^+$ (present) CSCs were stained with red Qdots, and the ALDH$^-$ (absent) non-CSC cells with green Qdots. The cells were mixed 1:1 and exposed to peptoid library beads (FIG. 3A). Only the red cell-bound beads were picked (FIG. 4A-C), as they indicated that the peptoid on that bead had bound to a biomolecule found only on the CSCs. This assay identified three distinct 8-mer peptoids: PCS1 and PCS2 from an initial peptoid library, and PCS3 from another peptoid library.

Figure 5A:
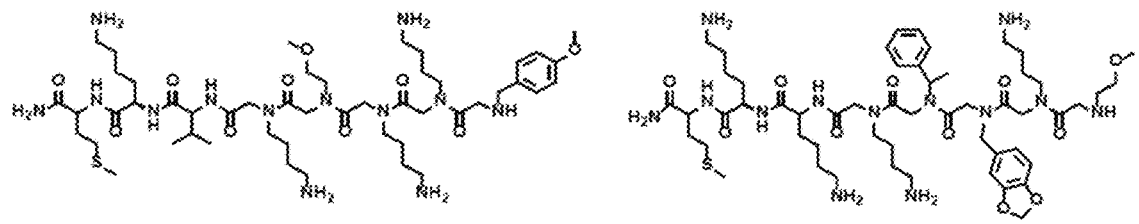
FIGS. 5A and 5B show the chemical structures.
Figure 5A:
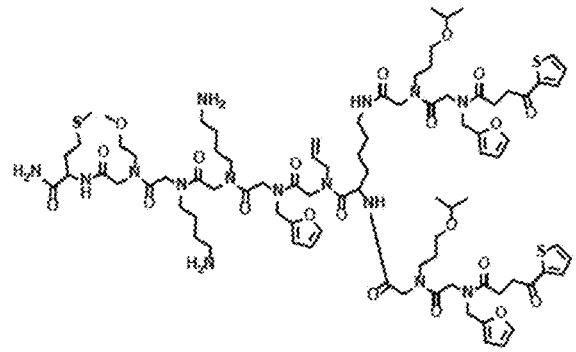
Figure 5A:
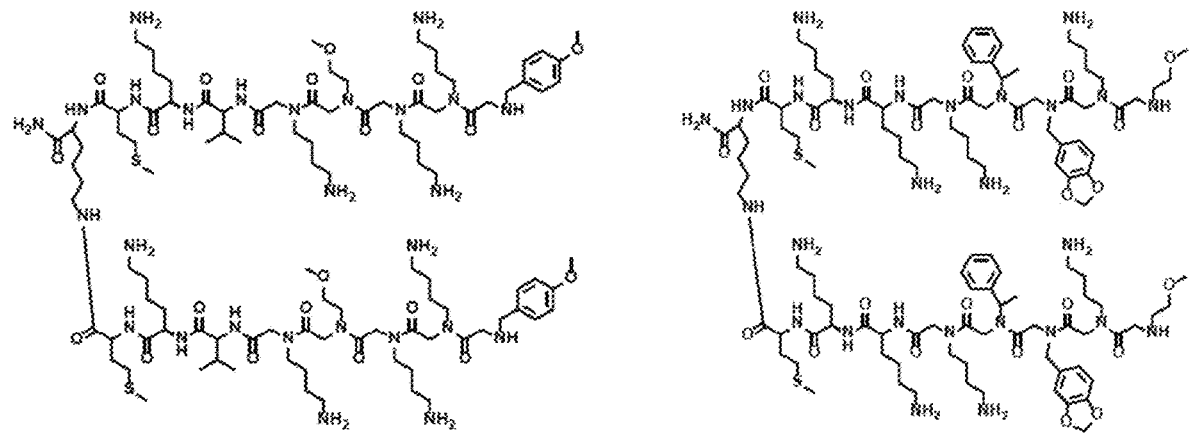

Three peptoids that bind specifically to a CSC fraction of H358 cells were identified. The chemical structure of each peptoid is shown (FIG. 5), along with PCS1D1 and PCS2D1, the homodimer variants of PCS1 and PCS2 (FIG. 5A), and extended series of PCS2 dimers PCS2D2.1, PCS2D2.2, PCS2D2.3, PCS2D2.4, and PCS2D2.5 (FIG. 5B) respectively, which show increased inhibitory effect over their respective monomers.

Example 2

Synthesis of Peptoid-Carrying Beads

Peptoid compound synthesis on tentagel beads: Each of the three peptoids (PCS1, PCS2, PCS3) were synthesized by Fmoc-based solid-phase peptide synthesis and microwave-assisted peptoid synthesis, for the peptide and peptoid sections, respectively, on 200 mg Tentagel MB NH2 bead (Rapp-Polymere, Germany) for the on-bead assay, and on Novasyn TGR resin (Millipore, Billerica, MA) for all other assays. All peptide-coupling steps were performed by mixing an Fmoc-protected amino acid (5 n)(Sigma) with coupling reagents [HBTU (4.9 n)(Sigma), HOBt (5 n)(Sigma), DIPEA (10 n)(Sigma)] in DMF (Dimethylformamide, Sigma) using disposable syringes gently shaken for 2 hours. Fmoc removal was done by 20% (v/v) piperidine (Sigma) in DMF, twice with 15 minutes gentle shaking. For peptoid additions, each peptoid unit was coupled in two reactions using microwave-assisted synthesis. Beads were treated with 2 M bromoacetic acid (Sigma) and 2 M DIC (Sigma) for 15 seconds at 100 W in the microwave, twice. This was followed by a wash five times with DMF, then two times with DCM (Dichloromethane, Sigma), then five times with DMF. Beads were treated with 2 M primary amine (Sigma) coupled using 15 seconds at 100 W in the microwave, twice. The molecular mass and purity of each compound was confirmed using an Applied Biosystems Voyager MALDI-TOF mass spectrometer, purified using a Waters HPLC, and lyophilized in a Benchtop SP Scientific Lyophilizer.

Magnetic bead coating with peptoids: Peptoids were synthesized with an additional cysteine at the C-terminal of the sequence. Maleimide-biotin was coupled through this cysteine to biotinylate the compound. Streptavadin-dynabeads (Thermo Scientific, Waltham, MA) were coated with biotinylated compound by vortexing the two together in PBS and then separated from the supernatant with a magnet. The peptoid-coated beads can then be used in cell-binding and pulldown assays, with a magnet used in the separation steps.

On-bead binding assay: 50 mg of peptoid-carrying tentagel beads or $1.3 \times 10^6$ of peptoid-carrying magnetic beads were equilibrated in 2 mL RPMI containing 5% FBS and 3% BSA (Sigma) for 1 hour by shaking. The beads can then be equilibrated with $5 \times 10^6$ of each cancer cell type listed above in 2 mL RPMI containing 5% FBS and 1% BSA at room temperature for 15-60 minutes for binding. The cell-bound beads are then pulled down with a magnet and washed with RPMI to cleanly harvest bound cells. Unbound cells were collected separately for further confirmations.

Example 3

Confirmation of Specificity to CSCs

Figures 4A, 4B, 4C, 4D, 4E, 4F, 4G:
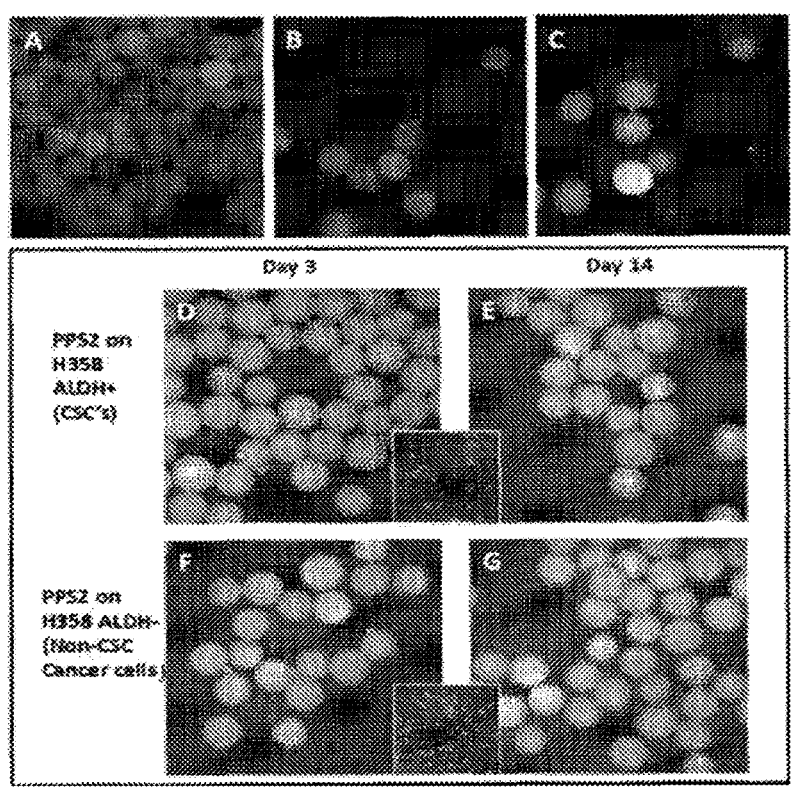
FIGS. 4A-C are microscopic views of three different peptoid beads bound only by red-colored cells, which are ALDH$^+$ (CSC) derived from lung cancer H358 cells.
FIGS. 4D and 4F are microscopic views of PCS2 peptoid beads binding only to sorted ALDH+ cells (CSC) but not to ALDH− cells.
FIGS. 4E and 4G are microscopic views of PCS2 peptoid beads binding only to sorted ALDH+ cells (CSC) but not to ALDH− cells, after allowing these CSC population to grow for 2 weeks

To confirm the binding specificity of PCS2 to CSCs, sorted ALDH+ H358 CSCs (red stained) and ALDH− H358 cells (green stained) were exposed to PCS2-carrying beads. PCS2-beads only bound significantly to the red CSCs (FIG. 4D & F). The same assay was repeated after allowing these CSC population to grow for 2 weeks, where by then the CSC percentage in the ALDH+ sorted population became low, the number of cells bound was very low (FIG. 4E), indicating PCS2 recognizes a unique target specific for CSCs, but not other cancer cells.

Figure 6A:
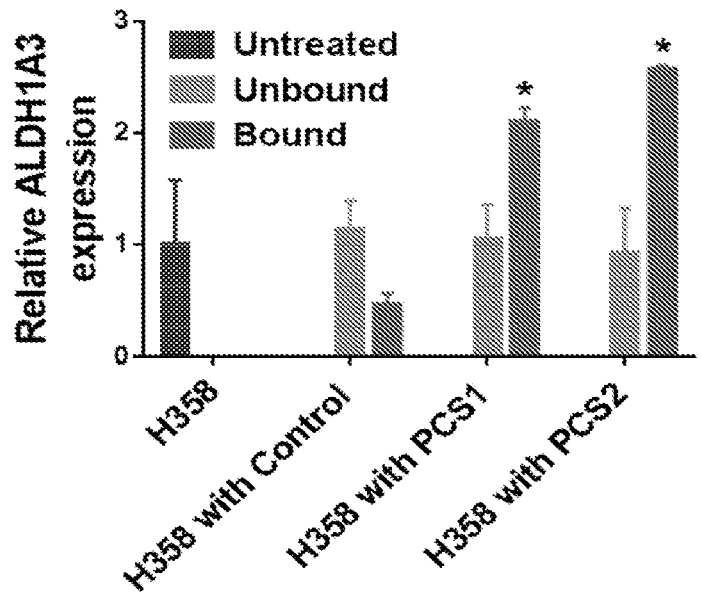
FIG. 6A is a graphical representation of ALDH1A3 mRNA levels of bound and unbound cells to PCS1, PCS2, and PCS3-carrying beads, and a control peptoid-carrying beads.

Further, H358 cells were exposed to PCS1-, PCS2-, and PCS3-coated magnetic beads, and then separated by magnet into peptoid-bound and peptoid-unbound fractions. RNA from both bound and unbound fractions was harvested and analyzed by RT-qPCR to determine the relative expression of ALDH1A3 in each subset of cells, compared to its expression in unbound H358 cells. In each case, expression of CSC marker ALDH1A3 was at least 2-fold higher than in the baseline cell line (FIG. 6A), indicating that the cells bound by the peptoid-coated-beads are ALDH+ CSCs.

Figure 6B:
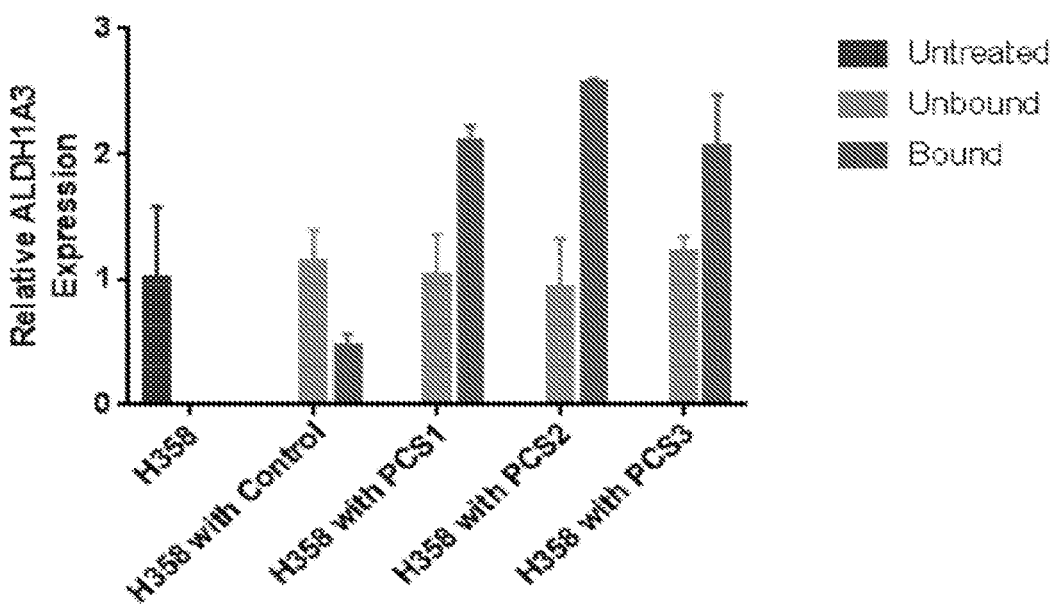
FIG. 6B is a graphical representation of SOX2 mRNA levels in H358, HCC4017, H366 and H460 cells that are either untreated, unbound (did not bind to PCS2-carrying beads), or bound to PCS2-carrying beads.

Using the same basic approach, peptoid-bound and peptoid-unbound fractions were generated from the lung cancer cells lines HCC4017, H358, H366, H460 for the PCS2 compound, and the relative expression of CSC marker SOX2 was evaluated between each fraction. In each case, the unbound fraction had increased expression of SOX2 compared to the unsorted or unbound fractions (FIG. 6B), indicating that the capacity of PCS2 to bind to CSCs is not exclusive to H358 cells.

Figures 7A, 7B, 7C:
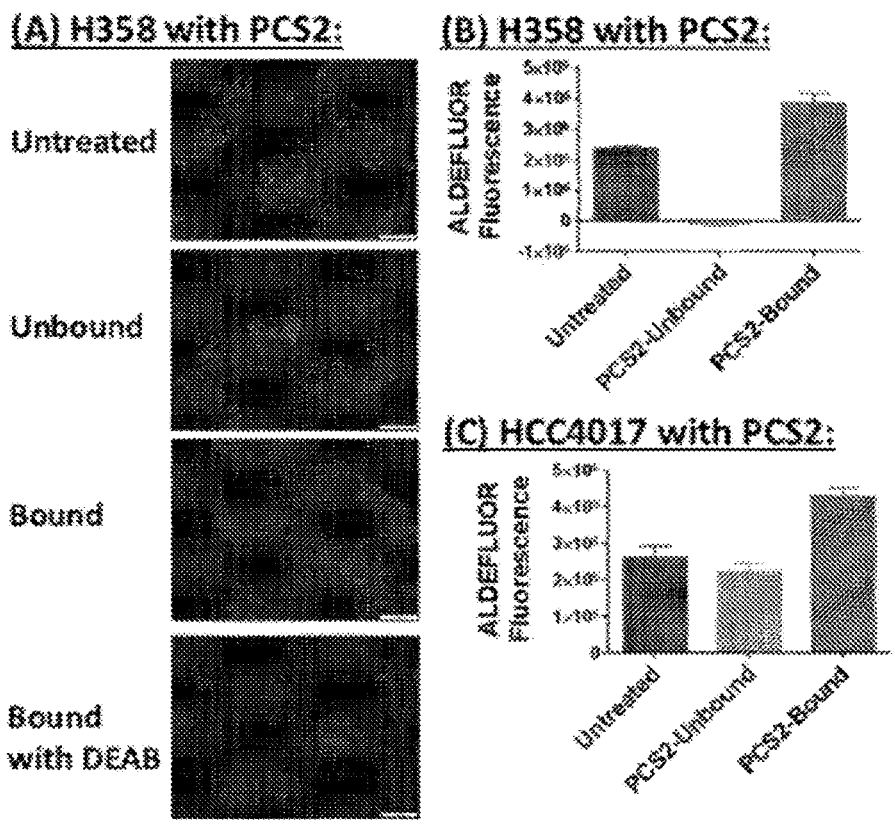
FIG. 7A is a set of microscopic views of cells sorted by PCS2-magnetic beads, demonstrating that the bound fraction has a higher number of ALDH+ cells and that this binding was reversible upon exposure to DEAB, an ALDH inhibitor.
FIG. 7B is a graphical representation of the ALDE-FLUOR fluorescence levels in H358 cells not treated with PCS2 beads, and in the treated H358 cells that form the bound and unbound fractions of cells bound to PCS2 beads.
FIG. 7C is a graphical representation of the ALDE-FLUOR fluorescence levels in HCC4017 cells not treated with PCS2 beads, and in the treated HCC4017 cells that form the bound and unbound fractions of cells bound to PCS2 beads.

To confirm that the peptoid-bound fraction was CSCs, a subset of PCS2-bound and PCS2-unbound fractions from H358 cells were generated and stained with the ALDEFLuor kit, which produces green fluorescence when the ALDH protein is active in a cell, and DAPI, and then analyzed them under a fluorescence microscope. The PCS2-bound fraction had a significantly stronger green fluorescence than both the unbound or untreated fractions, and this signal disappeared in the presence of ALDH inhibitor DEAB (FIG. 7A). An equal number of PCS2-bead sorted cells from the H358 and HCC4017 cell lines were also treated with the Aldefluor kit and their relative fluorescence was evaluated using a spectrophotometer (FIG. 7B & C). In each cell line, fluorescence was higher in bound cells than in unbound or untreated cell counts, showing that the ALDH subset was present in the bound cells.

Figure 8:
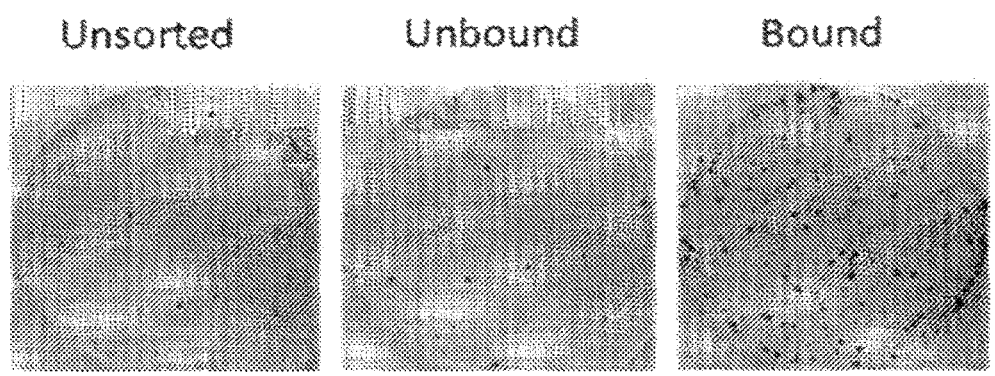
FIG. 8 is a series of photographs of plates showing the different potentials for colony formation of cells sorted by PCS2-magnetic beads and unsorted cells; shown is a photograph of a plate showing the colony forming potential of unsorted cells, a photograph of a plate showing the colony forming potential of cells in the unbound fraction when sorted by PCS2-magnetic beads (very few), and a photograph of a plate showing the colony forming potential of cells that bound to PCS2-magnetic beads (very high).

A colony formation assay was performed on the untreated H358 cells and PCS2-bound and PCS2-unbound fractions to further confirm that the cells bound by PCS2 were CSCs. About 500 cells from each of the three fractions were plated into 35 mM wells and grown for 2 weeks. The resulting colonies were then stained with crystal violet. A significantly higher number of colonies grew from the PCS2-bound fraction than either the unbound or unsorted H358 fractions (FIG. 8), indicating that the PCS2-bound cells have a significantly higher colony-forming potential.

To further evaluate the binding capacity of the three peptoids, 17 lung cancer lines and two normal lung epithelial lines (HBEC30KT and HBEC3KT) were exposed to magnetic beads coated with each of the three peptoids. The binding affinity of each cell line-peptoid combination was evaluated based on the number of cells that bound to beads (FIG. 9). While the percentage of cells pulled down by each peptoid varied in each line, each peptoid had a distinct subset of cancer lines they bound to and did not bind to, indicating that all three peptoids have the capacity to bind to CSCs in multiple cancer lines, and each peptoid likely has a distinct molecular target. To show that this interaction is not specific to the magnetic beads, the same assay was performed using PCS2-tentagel beads, and these beads had similar binding potential to the PCS2-magnetic beads with the overall cancer line library.

Example 4

Confirmation of Functional Effect of PCS2D1

Figure 10:
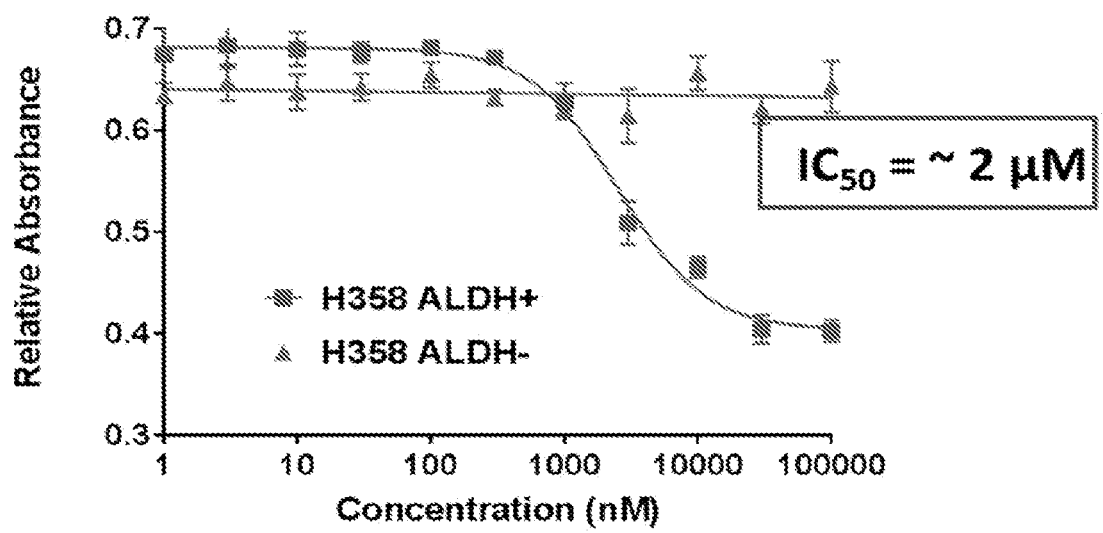
FIG. 10 is a graphical representation of the MTS cytotoxicity assay of PCS2D1 treatment on H358 ALDH+ cells and H358 ALDH− cells.

To verify that PCS2-treatment has a direct effect on the survival of CSCs, an MTS survival assay was performed on sorted H358 cells. The assay is based on the reduction of MTS tetrazolium compound by viable cells to generate a colored formazan product that is soluble in cell culture media. This conversion is thought to be carried out by NAD(P)H-dependent dehydrogenase enzymes in metabolically active cells. The formazan dye produced by viable cells was quantified by measuring the absorbance at 490-500 nm. H358 cells were stained using the ALDEFluor, then the ALDH+ cells were isolated by the MD Anderson Flow Cytometry and Cell Sorting core. The sorted ALDH+ cells were treated with 1 nM to 100 µM of PCS2D1 for 24 hours, and then the relative amount of surviving cells was determined by MTS. The number of cells in the ALDH+ fraction decreased under the treatment of PCS2D1, while ALDH− cells were unaffected (FIG. 10). The $IC_{50}$ was around 1 µM, which is very significant as targeting highly active CSC is a daunting task. Furthermore, this peptoid is still at the initial stage of development and further modifications can be made to optimize and increase the potency. This indicates that PCS2-treatment has a direct effect on CSC survival, but no significant effect on the non-stem-like cancer cells.

Figure 11A:
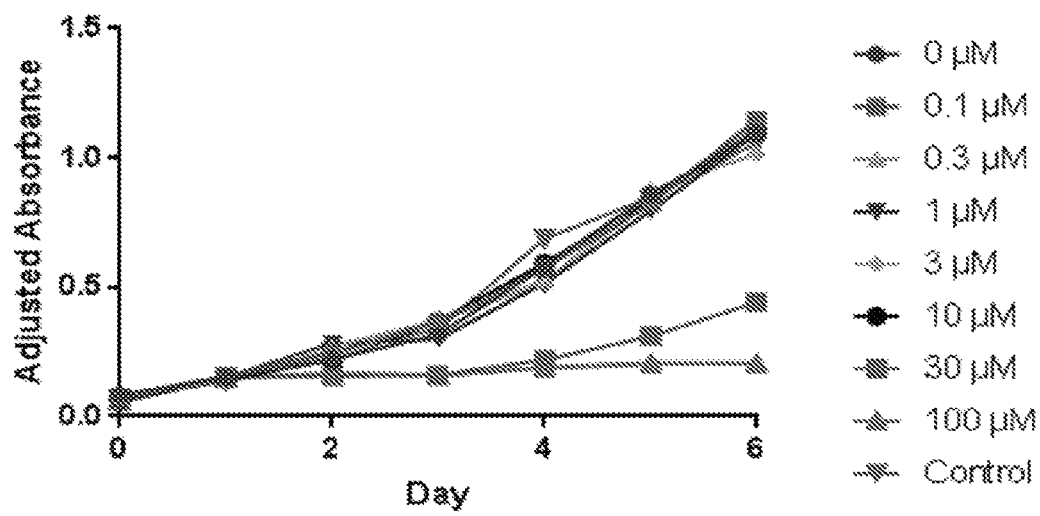
FIG. 11A is a graphical representations of the MTS cytotoxicity assay of PCS2D1 treatment (in increasing concentrations) on H358 unsorted cells.
Figure 11B:
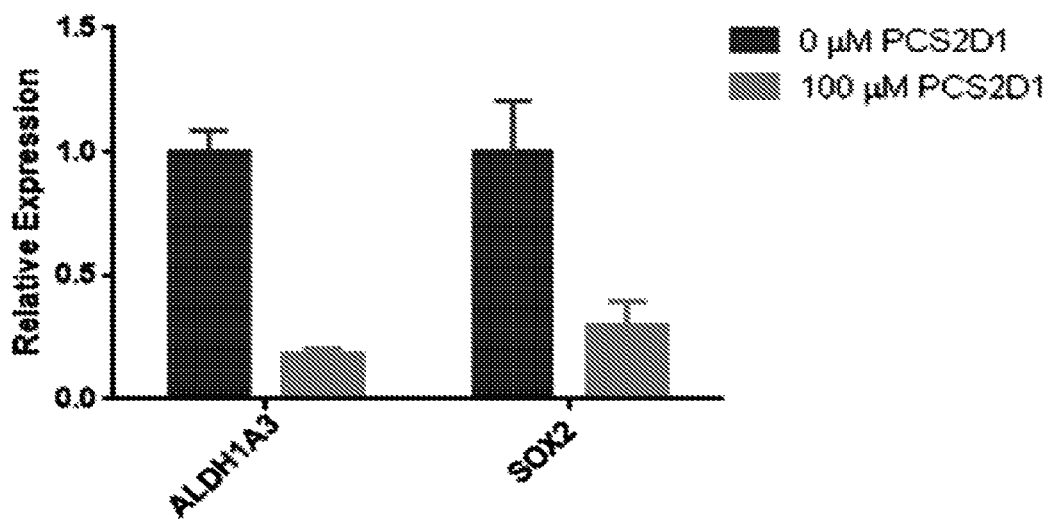
FIG. 11B is the analysis of cancer stem cell biomarkers on treated cells, where all those markers are reduced.

Further experiments were conducted to evaluate how PCS2 affects the proliferation of unsorted cancer cell populations. The standard MTS cell-proliferation assay was performed on unsorted H358 cells (known to contain 5-15% of CSCs) and measured proliferation rates over 6 days, at concentrations ranging from 100 nM to 100 µM of PCS2D1. Interestingly, PCS2D1 at concentrations of 30 µM and higher significantly decreased the overall growth of the H358 cell line by day 2 (FIG. 11A), with no significant growth observed at 100 µM. Furthermore, the cells treated with 100 µM of PCS2D1 were tested for expression of CSC markers ALDH1A3 and SOX2 after 96 hours of treatment, there was a significant drop in the expression of each one of those genes (FIG. 11B). This indicates that PCS2-treatment may have reduced the numbers of ALDH1A3- and SOX2-expressing CSCs, causing an overall decrease in cell growth.

Figures 12A, 12B:
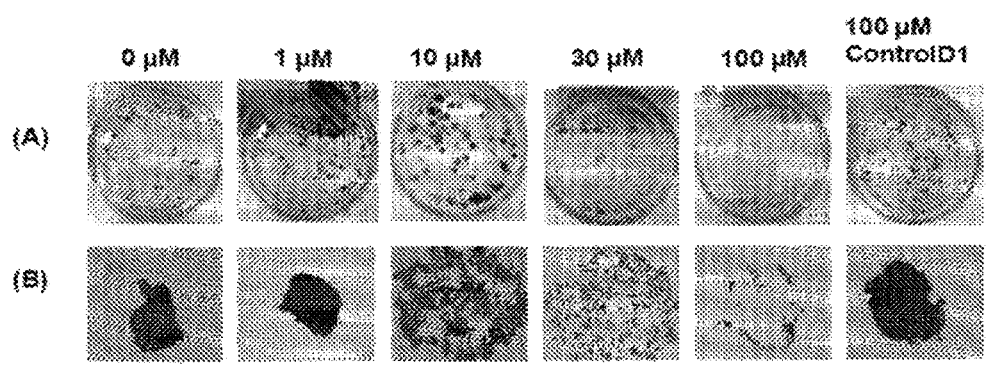
FIG. 12A is a set of photographs of H358 colonies, where the colony formation potential is reduced after two weeks of PCS2D1 treatment (in increasing concentrations).
FIG. 12B is a set of photographs of the morphology of a single colony formed by H358 cells after two weeks of PCS2D1 treatment (in increasing concentrations).

To further validate that PCS2D1 inhibiting CSCs, the effects of PCS2D1 against a stem-cell-associated phenotype were studied with regards to the capacity to form colonies from a single cell by using the clonogenicity assay. About 300 cells were plated onto 35 mm cell culture plates with either 0, 1, 10, 30, or 100 μM of PCS2D1, and allowed to grow for 2 weeks. After staining with crystal violet, both the number of colonies and the overall morphology of the colonies were evaluated. While both 30 and 100 μM treatments show a significant decrease in colonies formed (FIG. 12A), at 10 μM the morphology of the colonies changes drastically, showing significantly more dispersed colonies (FIG. 12B), with the morphology getting more dispersed as the concentration increases. This indicates that treatment with PCS2D1 reduces the colony-forming potential in H358 CSCs.

Figures 13A, 13B, 13C:
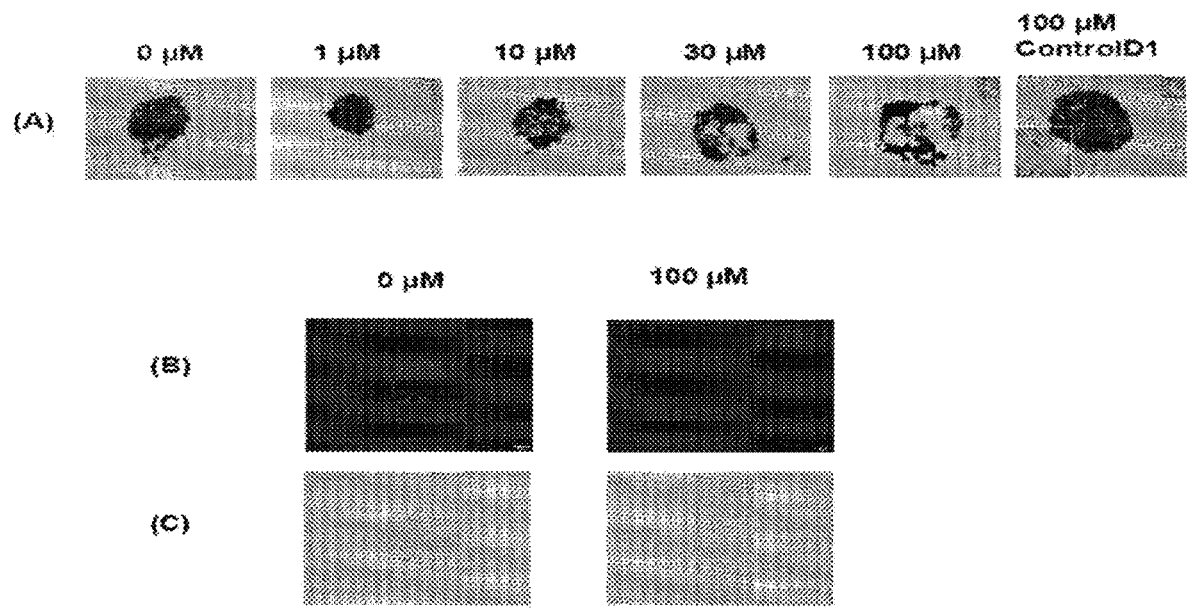
FIG. 13A is a set of photographs of the morphology of a single colony formed by H358 cells after one week of PCS2D1 treatment (in increasing concentrations).
FIGS. 13B and 13C are ALDH fluorescent microscopic views and Brightfield microscopic views respectively, of the same single colony formed by H358 cells after one week of PCS2D1 treatment (100 µM).

Another set of experiments were designed to evaluate if differentiated cells from CSCs were targeted by PCS2D1 as well. A variation of the clonogenicity assay was performed, where about 300 unsorted H358 cells were plated to 35 mm plates each and allowed to form colonies for 7 days. After that time, the colonies were treated with either 0, 1, 10, 30, or 100 μM of PCS2D1 for 24 hours, and then stained with crystal violet. The colonies were examined under a microscope. After treatment with 10 μM, the colonies show significant loss of cells from the colony center, with the number of cells lost increasing at higher concentrations (FIG. 13A). To determine if the cells lost are CSCs or the differentiated cells, ALDEFluor staining was performed against some of the colonies at 0 and 100 μM treatment. In the untreated cells, the colonies show a significant ALDH fluorescence, while the cells treated with 100 μM show no significant fluorescence (FIGS. 13B-13C). This indicates that PCS2D1 binds and inhibits CSCs, but does not appear to have an effect on even recently differentiated cells.

Figures 14A, 14B, 14C:
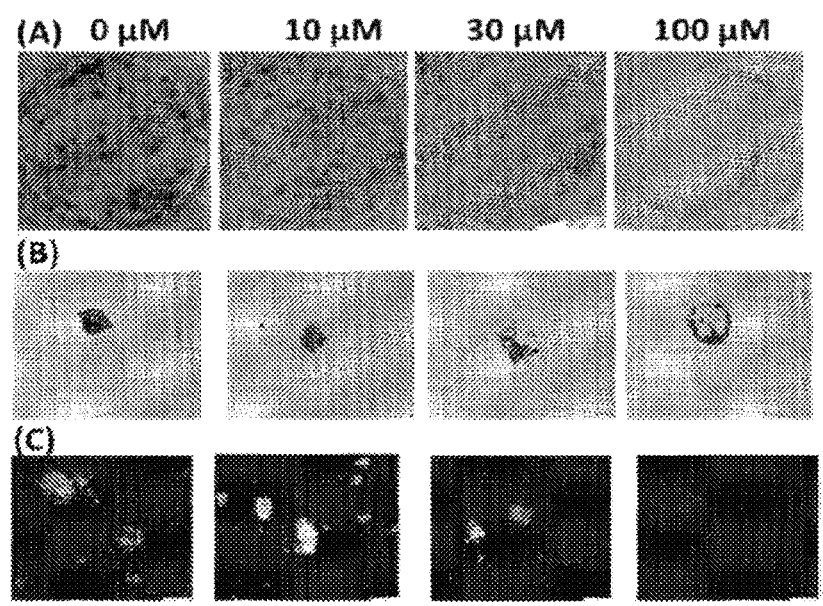
FIG. 14A is a set of photographs of the colony formation potential of H358 cells after two weeks of PCS2D1 treatment (in increasing concentrations).
FIG. 14B is a set of photographs of the morphology of a single colony formed by H358 cells after one week of PCS2D1 treatment (in increasing concentrations).
FIG. 14C is a set of ALDH fluorescent microscopic views which indicates high PCS2D1 treated colonies loss ALDH staining, indicating cancer stem cells are affected.

The clonogenicity assay was repeated with H358 cells, 500 cells/well, using 0, 10, 30 and 100 μM PCS2 treatment over 2 weeks. Significantly fewer colonies formed in the 30 and 100 μM treatment groups (FIG. 14A). To confirm that this was due to the specific targeting on CSCs, the clonogenicity assay was performed again over 8 days, with the treatment performed from day 7 to 8 instead, to allow the colonies to establish. This was done alongside control cells plated on chamber slides and then grown under the same conditions. The colonies remained present following treatment with 10-100 μM of PCS2D1 but showed a significant loss of "central" cells (FIG. 14B) that are typically CSCs. Staining with the Aldefluor assay showed a reduction in fluorescent cell number at 10-30 μM and a complete loss of ALDH$^+$ cells in the 100 μM treatment group (FIG. 14C), implicating that CSC cells and not differentiated cells are targeted by PCS2.

Figure 15A:
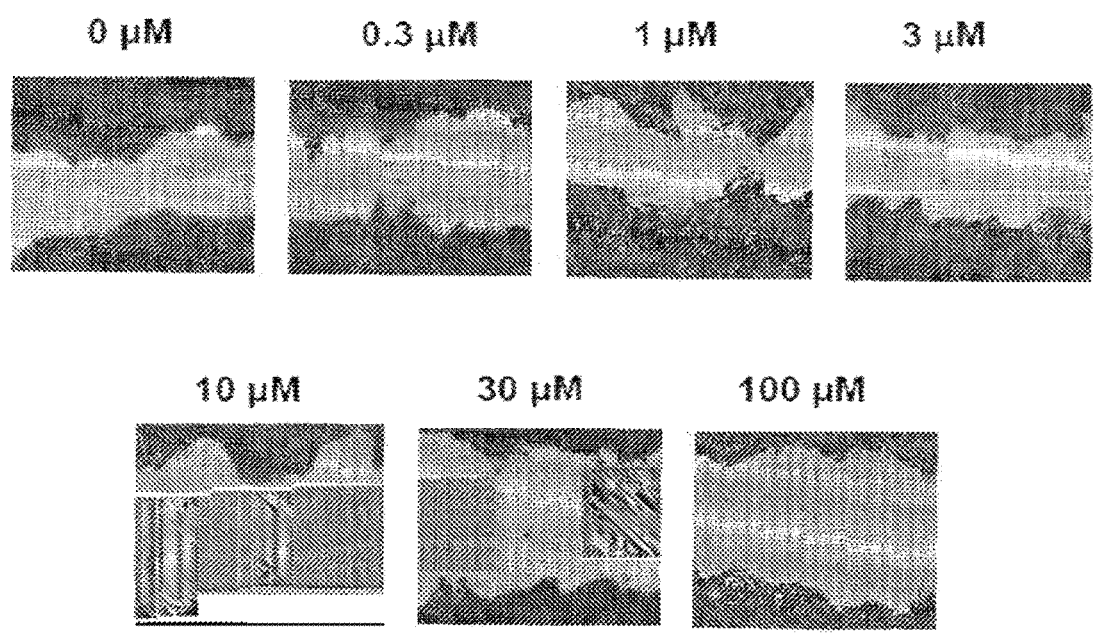
FIG. 15A is a set of photographs of the scratch assay performed using H358 cells after 24 hours of PCS2D1 treatment (in increasing concentrations).
Figure 15B:
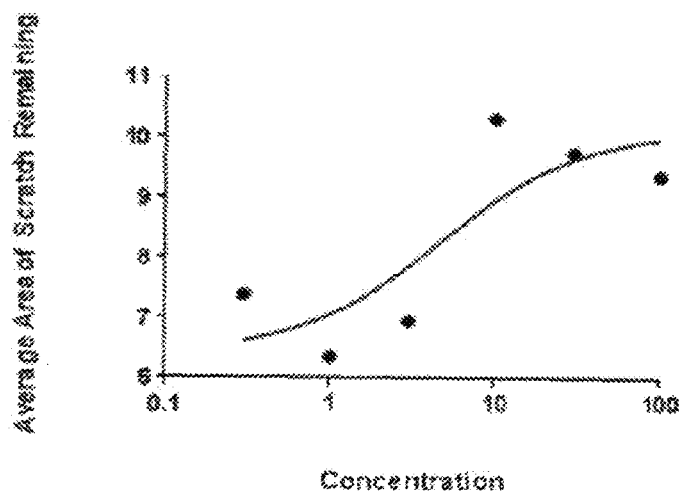
FIG. 15B is a graphical representation of the average area of the remaining scratch from the scratch assay performed using H358 cells after 24 hours of PCS2D1 treatment (in increasing concentrations).

Another stem-cell-associated phenotype is the capacity of stem cells to migrate and repair gaps in a tissue or cell culture. To determine if this capacity is affected by PCS2D1, a scratch (would healing) assay was performed on H358 cells after 24 hour treatment of 0, 0.3, 1, 3 10, 30 or 100 μM of PCS2D1. Each well of confluent H358 unsorted cells was scratched using a 1000 μL pipet tip, washed, then treated with PCS2D1 for 24 hours. Each well was then stained, and the average area of the remaining scratch was calculated from a microscope viewing window near the center of the well. At 10 μM and higher treatments, migration was significantly inhibited (FIG. 15A), as noted by the significant increase in width and area of the scratch remaining compared to the below-10 μM scratches (FIG. 15B). This indicates that PCS2D1 inhibits migration potential of H358.

PCS2-coated beads bound strongly to a large subset of cells multiple lines, and the cells isolated had higher SOX2 expression compared to the unbound or untreated cells. The cells isolated by PCS2 binding also had increased colony-formation potential, implicating that PCS2 is binding to a more stem-like subpopulation of cells. PCS2 treatment significantly decreased the cell growth of the treated cells. Significantly, lower expression of ALDH1A3 and SOX2 in the treated cells implicates that is likely due to a loss of a stem cell subpopulation. Treatment using PCS2 inhibited colony formation potential in H358, and, if colonies are allowed to form in a drug-free environment, the outlying cells, likely more differentiated, were not affected by the treatment. This implicates that PCS2 functions as an inhibitor for only a stem-like subset.

Example 5

Identification of a PCS2 Target Protein as Plectin

PCS2 was used in further cross-linking, pulldown and standard proteomics studies to identify its targeted biomarkers in CSC. One target that was isolated was the protein—Plectin. This protein is known to be found in some cancers, but never has been reported or linked as a biomarker for CSCs.

Bead preparation: About 10 μL of 100 μM PCS2 was added to $2*10^6$ magnetic beads in 0.1% BSA/PBS (500 μL per $2*10^6$ beads). This mixture was incubated on a shaker for 30 minutes at room temperature. This process can be scaled up if one needs more than more than $2*10^6$ cells. The beads are then washed three times with 0.1% BSA solution, and isolated using a magnet.

Sort compound binding cells: About $2*10^6$ cells are resuspended in 3% BSA/5% FBS/RPMI (500 μL), and added to the isolated beads. This mixture was incubated for 10 minutes at room temperature. The beads were washed six times in 5% FBS/RPMI.

Crosslink benzophenone to target: The beads were resuspended in PBS or 0.1 M Tris buffer and placed in an ice bath. This step was followed by exposure for an hour to UV light (UV-A, 365 nm). The beads were then isolated using magnets.

Lysis: Mild lysis buffer was added to the beads, followed by a thirty minute incubation of the mixture at 4° C. The beads were isolated and the lysate removed. The beads were resuspended in RIPA or 0.1% SDS buffer, boil 10 minutes to denature the streptavidin. The liquid containing the isolated targets was removed and subject to further processing for analysis by Western Blotting and MS. Samples were subject to separation on a 4-12% gel that was stained with Silver Stain, and the unique bands were further analyzed by mass spectrometry. For Western blotting analysis, the contents of the gels were transferred to a membrane (using high MW conditions) and probed with antibodies appropriate to potential targets. The proteins were visualized using secondary antibodies through a ScanLater Europium detection method.

Figure 16:
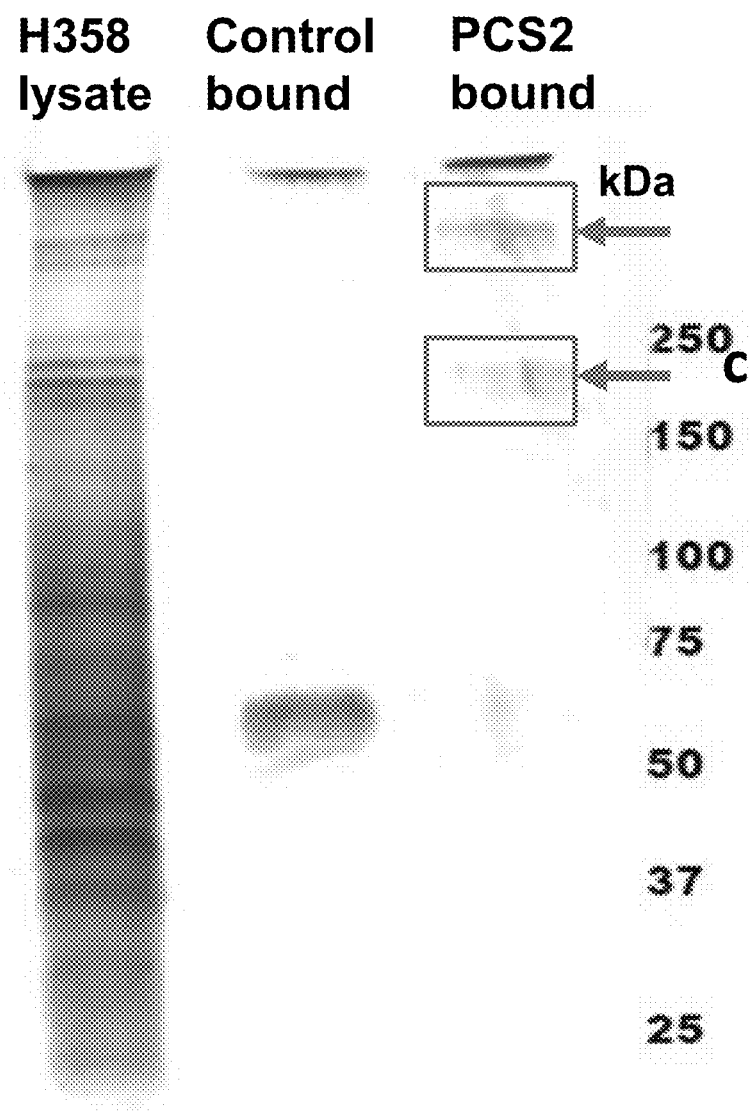
FIG. 16 is a visualization of a silver stained gel showing the protein profile of bound cell surface proteins to the PSC2D1 coated beads, pulled down after exposed and cross-linked to H358 cells

FIG. 16 is a visualization of a silver stained gel showing the protein profile of bound proteins to the PSC2-beads. The two bands indicated with arrows were excised and subject to directed proteomics analysis at the MD Anderson Proteomics Core facility by Dr. David Hawke. Mascot search results indicated that one of the target proteins isolated through the binding studies to the PCS2-beads was human plectin.

Figure 17:
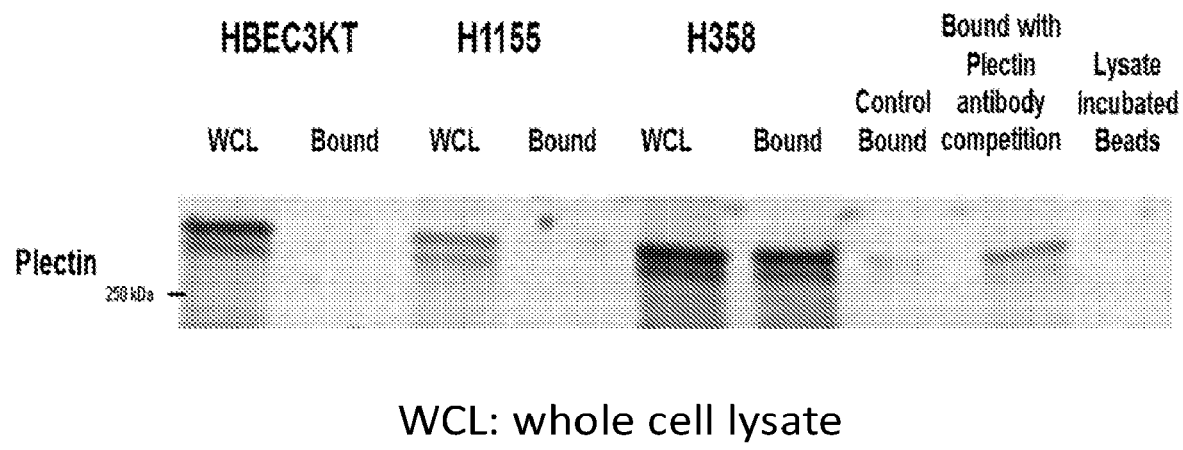
FIG. 17 is a visualization of a gel stained with showing the protein profile of bound proteins from H358 cells (high PCS2 binding/cancer), H155 cells (low PCS2 binding/cancer) and HBEC3KT cells (low PCS2 binding/normal) to the PSC2-beads and reactive to anti-Plectin antibody competition.

The interactions between PCS2 and plectin were further confirmed in a series of experiments. First, H358 cells (high PCS2 binding/cancer), H155 cells (low PCS2 binding/cancer) and HBEC3KT cells (low PCS2 binding/normal) were exposed to bead-bound PCS2 and the cell surface proteins bound to the PCS2-beads were separated using acrylamide gel electrophoresis. Then the gel was analyzed using a ScanLater Western Blot Kit containing europium-labeled secondary antibodies designed to work with anti-plectin antibodies. FIG. 17 is a visualization of a gel showing the protein profile of bound proteins to the PCS2D1-beads and reactive to Anti-Plectin antibody (1:1000). Additionally, commercially available Plectin antibody was used to compete off the PCS2-beads on H358 cells (lane 8, FIG. 17).

Figure 18:
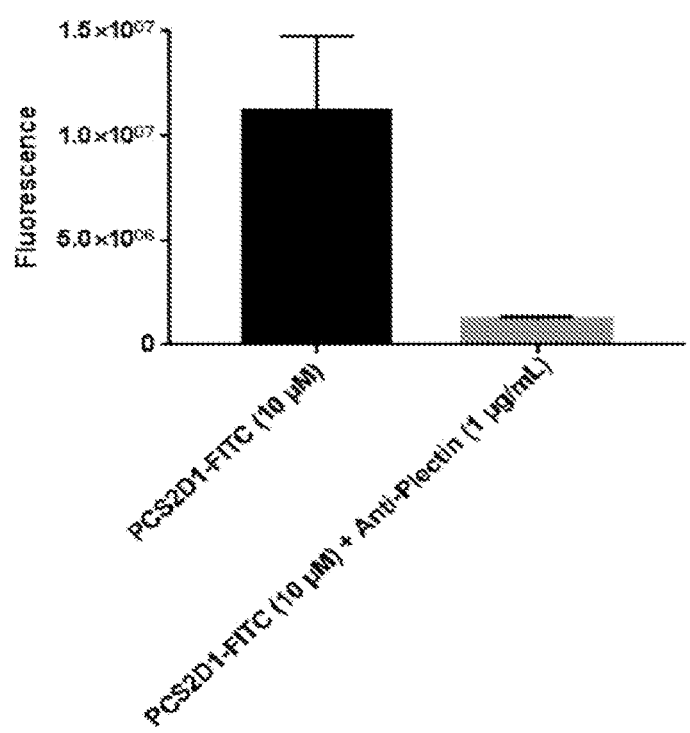
FIG. 18 is a graphical representation of the binding of FITC-PCS2 peptoids to CSCs when the CSCs were either untreated or treated with anti-Plectin antibodies.

Second, about 5000 ALDH+ CSCs per well were plated on 96-well plate. Then, 1% BSA in PBS was added to each well and incubated for an hour to eliminate interference and minimize background noise. The cells were washed with PBS three times and then incubated for an hour in the presence of anti-Plectin 1 µg/mL. The cells were washed with PBS three times and then incubated for an hour in the presence of PCS2D1-FITC (10 µM). The cells were washed with PBS three times and the FITC fluorescence in each of the wells was quantified. FIG. 18 is a graphical representation of the binding of FITC-PCS2 peptoids to CSCs when the CSCs were either untreated or treated with anti-Plectin antibodies. Fluorescence decreased when the cells were treated with anti-Plectin antibody, implying competition: decreased binding of compound in the presence of the antibody.

Based on Examples 1-5, it was determined that PCS1, PCS2, and PCS3 are novel peptoid compounds that preferentially target CSCs. These compounds enriched CSC's by binding to CSC subsets from a large panel of lung cancer cell lines, but not to remaining cancer cells as well as to normal bronchial epithelial cells. Furthermore, PCS2 has been shown to inhibit cancer cell growth, proliferation, wound healing, and colony formation. These peptoids have the capacity to be developed into a novel identification and sorting method for a CSC-subpopulation in tumors. These peptoid drug leads have the strong potential to be developed into CSC-directed therapeutics, which could have a considerable impact on patient survival. In addition, the advantageous properties of these peptoids, such as their high serum stability, cell permeability, non-immunogenicity, and their simple and cost-effective synthesis make them highly promising candidates for drug development. Moreover, the selected peptoids bind to biomarkers specific for CSCs. As the peptoids are specific for CSC, PCS1, PCS2 and PCS3, they can be used to isolate CSC from a tumor and/or tissues like the blood. These peptoids can also be used as diagnostics for the presence of CSC as part of initial cancer diagnosis or for detecting the presence of CSC following treatment with anti-cancer therapeutics.

Example 6

Confirmation of Specificity to CSCs

Figure 19A:
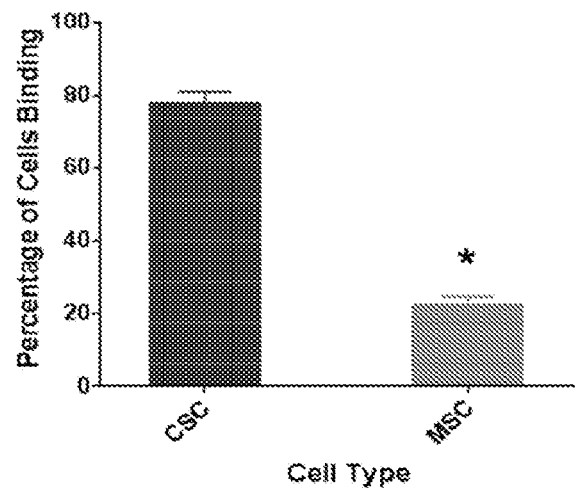
FIG. 19A is a graphical representation of the relative binding affinity of CSCs isolated from H358 cancer cells and normal mesenchymal cells treated with PCS2 beads.
Figure 19B:
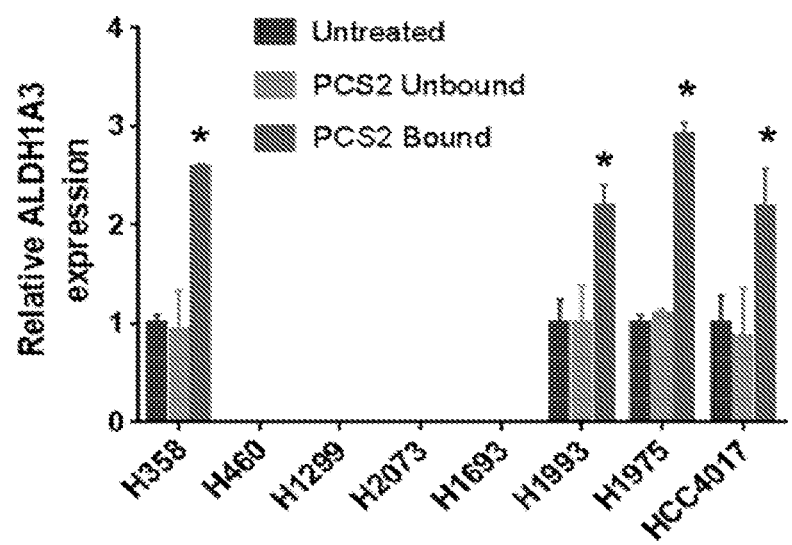
FIG. 19B is a graph showing the relative expression of ALDH1A3 mRNA levels in each of several lung cancer cell lines fractions.
Figure 19C:
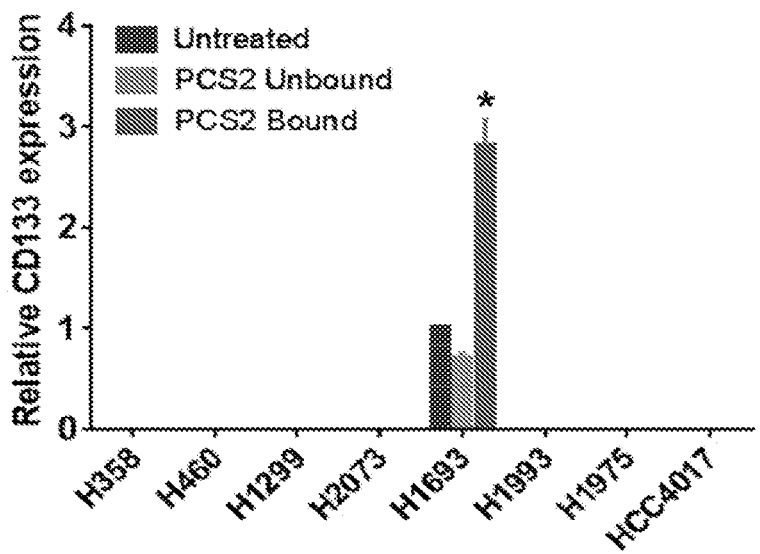
FIG. 19C is a graph showing the relative expression of CD133 mRNA levels in each of several lung cancer cell lines fractions.
Figure 19D:
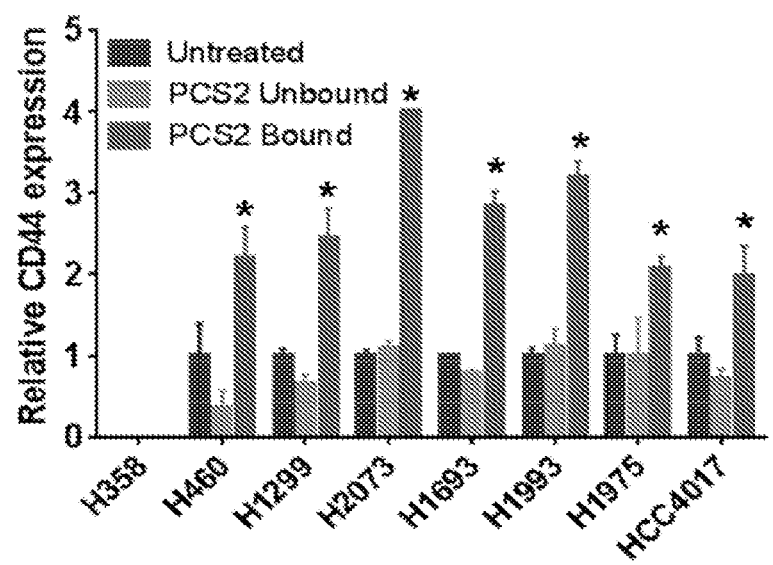
FIG. 19D is a graph showing the relative expression of CD44 mRNA levels in each of several lung cancer cell lines fractions.
Figure 19E:
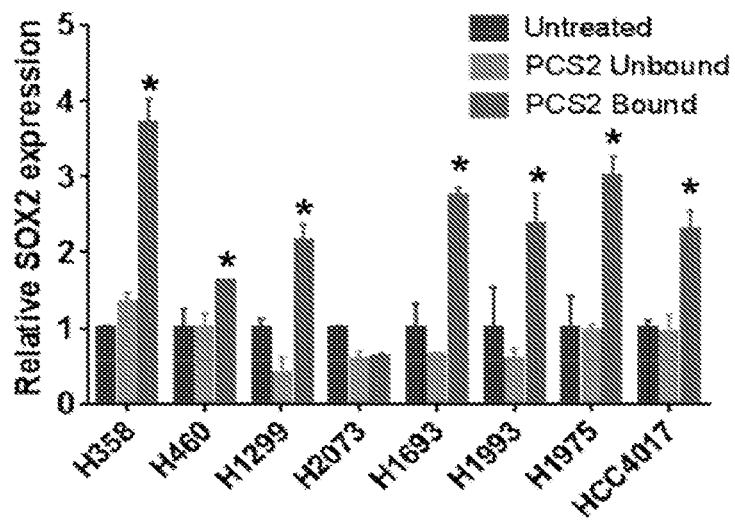
FIG. 19E is a graph showing the relative expression of SOX2 mRNA levels in each of several lung cancer cell lines fractions.

To confirm the binding specificity of PCS2 to CSCs, CSCs isolated from H358 cells and normal mesenchymal stem cells (MSCs) were exposed to PCS2-carrying beads as described in Example 3, and then separated by magnet into peptoid-bound and peptoid-unbound fractions (FIG. 19A). PCS2 was bound significantly higher on CSCs from H358 than normal MSCs, indicating high specificity towards CSCs over normal stem cells (current CSC targeted compounds are targeting normal stem cells as well giving high non-specific side effects). To further evaluate PCS2 specificity towards CSCs, HCC4017, H460, H1299, H2073, H1693, H1993, and H1975 cells were exposed to PCS2-carrying beads, and then separated by magnet into peptoid-bound and peptoid-unbound fractions. RNA from both bound and unbound fractions was harvested and analyzed by RT-qPCR to determine the relative expression of several known CSC biomarkers in each fraction was assessed, including expression of ALDH1A3 (FIG. 19B), CD133 (FIG. 19C), CD44 (FIG. 19D), and SOX2 (FIG. 19E). CD44 and SOX2 expressions were high on PCS2-coated magnetic-bead bound fractions from the almost all cell lines having higher expression of CSC biomarkers compared to the unsorted or unbound fractions confirming that the capacity of PCS2 to bind to CSCs is not exclusive to H358 cells. The correlation to ALDH1A3 and CD133 were varied, which is typical due to the high heterogeneity of CSC biomarker expressions, and there are no 100% biomarker correlations exists.

Figure 19F:
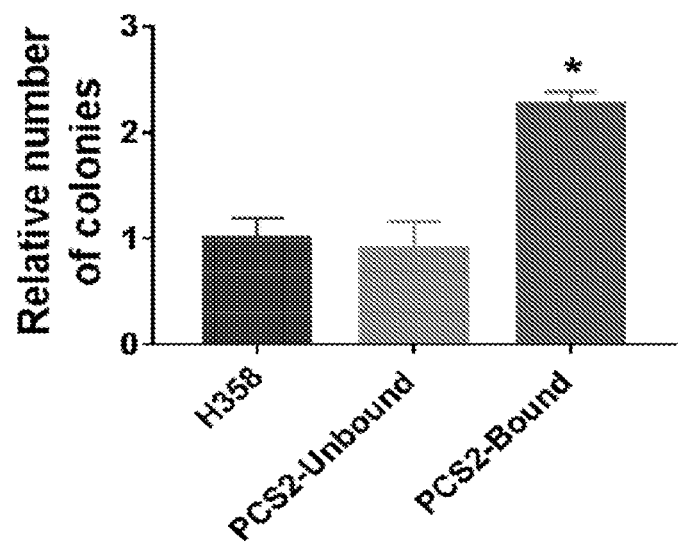
FIG. 19F is a quantified data graph showing H358 cells separated using PCS2-coated magnetic-beads formed significantly more colonies after 2 weeks of growth than unbound or untreated fractions, indicating PCS2 is pulling down cells with CSC-like characteristics.

A colony formation assay was performed on the untreated H358 cells and PCS2-bound and PCS2-unbound fractions to further confirm that the cells bound by PCS2 were CSCs. About 300-500 cells from each of cell group were plated into 35 mM wells and grown for 2 weeks or until colonies were visible by eye. The resulting colonies were then stained with crystal violet for approximately 5 minutes and colonies were counted using the MOESM software program, and confirmed though microscopic counting. A significantly higher number of colonies grew from the PCS2-bound fraction than either the unbound or unsorted H358 fractions (FIG. 19F), confirming that the PCS2-bound cells have a significantly higher colony-forming potential.

To further evaluate the binding capacity of the three peptoids, 17 lung cancer lines and two normal lung epithelial lines (HBEC30KT and HBEC3KT) were exposed to magnetic beads coated with each of the three peptoids. The binding affinity of each cell line-peptoid combination was evaluated based on the number of cells that bound to beads (FIG. 20). While the percentage of cells pulled down by each peptoid varied in each line, each peptoid had a distinct subset of cancer lines they bound to and did not bind to, confirming that all three peptoids have the capacity to bind to CSCs in multiple cancer lines, and each peptoid likely has a distinct molecular target.

Example 7

Further Confirmation of Functional Effect of PCS2

Figure 21:
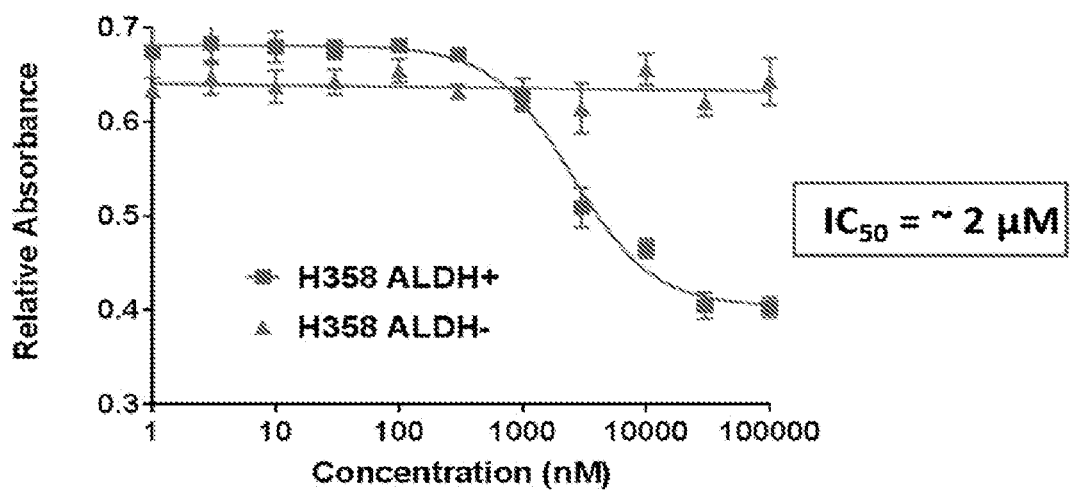
FIG. 21 is a graphical representation of the MTS cytotoxicity assay of PCS2D1 treatment on H358 ALDH+ cells and H358 ALDH− cells.

To verify that PCS2-treatment has a direct effect on the survival of CSCs, an MTS survival assay was performed on sorted H358 cells as described in Example 4. The number of cells in the ALDH+ fraction decreased under the treatment of PCS2D1, while ALDH− cells were unaffected (FIG. 21). The $IC_{50}$ was around 2 µM. This confirmed that PCS2-treatment has a direct effect on CSC survival, but no significant effect on the non-stem-like cancer cells.

Example 8

Plectin siRNA Knockdown

Unsorted H358 cells were plated on a 6-well plate and grown to 80% confluence. For each well, 9 µL of Lipofectamine RNAiMAX (Thermo Fisher) was mixed with 3 µL of 10 µM siRNA, either silencer select s10644 plectin or silencer select negative control 1 (Thermo Fisher), in serum-free RPMI and incubated for 5 minutes. The mixture was then added to the well and incubated for 1 to 4 days before testing. Magnetic binding assays were performed on harvested cells as described above for binding evaluation.

Figure 22A:
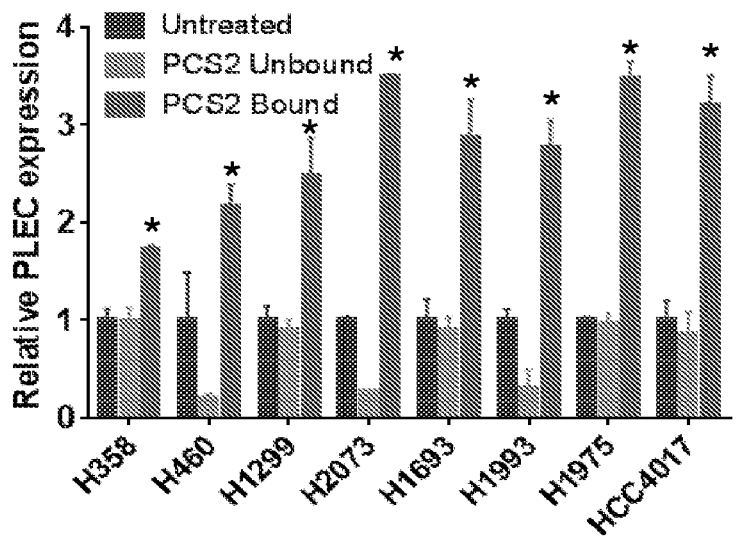
FIG. 22A is a graph showing the relative expression of PLEC mRNA in PCS2-bead isolated cells from several lung cancer cell lines.
Figure 22B:
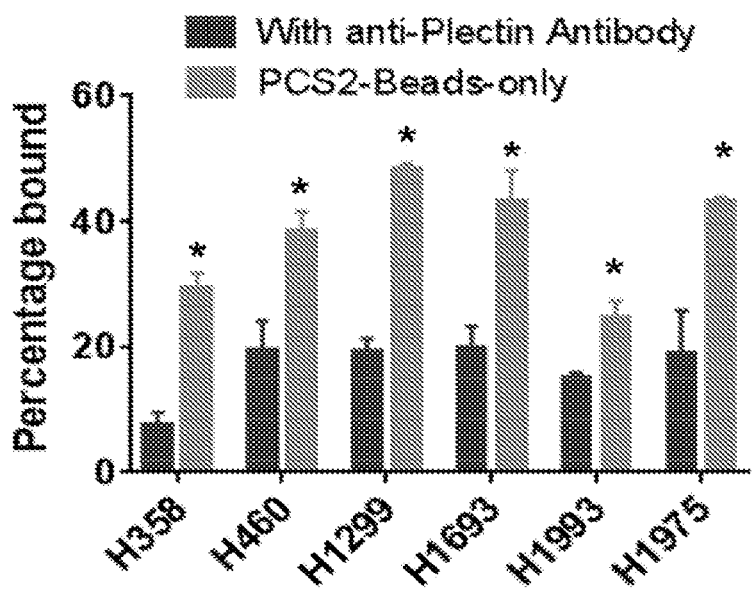
FIG. 22B is a graphical representation of the relative binding affinity of cells treated with PCS2 beads in the presence and absence of anti-Plectin Antibody. The drop of binding due to anti-plectin antibody competition strongly indicates that PCS2 is targeting plectin.
Figure 22C:
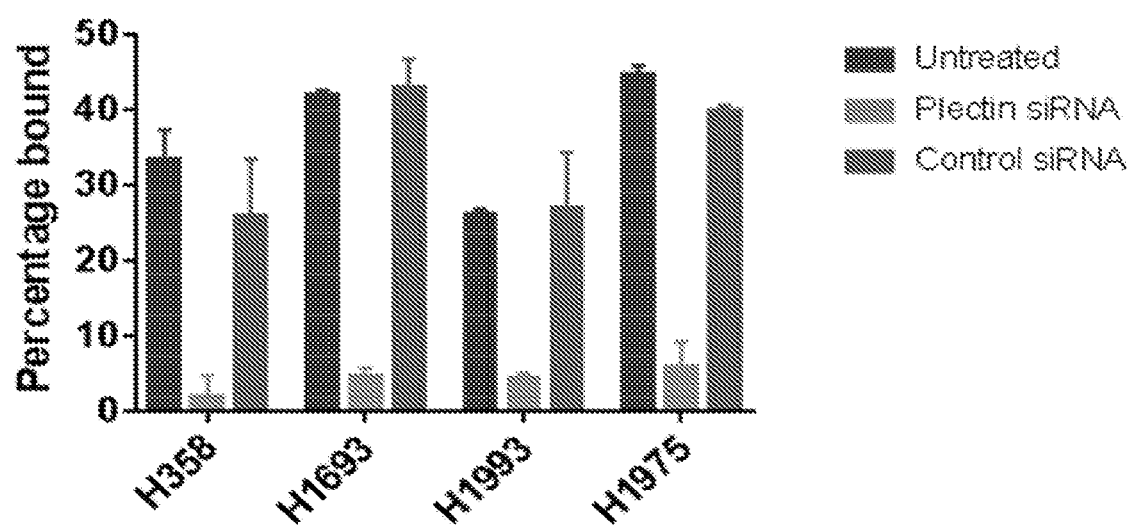
FIG. 22C is a graphical representation of the siRNA knock-down of plectin significantly decreasing the percentage of cells binding to PCS2-coated magnetic-beads in H358, H1693, H1975 and H1993 cells compared to no knockdown and control siRNA treated cells.

Plectin expression was directed tested on PCS2-bound cells from H358, HCC4017, H460, H1299, H2073, H1693, H1993, H1975 cells by RT-QPCR (FIG. 22A). While exact molecular details about PCS2 recognition on plectin is yet to be established, the antibody used during the competitive assay (FIG. 22B) is a C-terminal domain-targeting antibody and hence it was predicted PCS2 most likely binds somewhere within the C-terminal region of the plectin. Plectin expression was significantly higher in PCS2-bound cells than unbound cells of all lines tested (FIG. 22A). To determine if PCS2 and the plectin antibody compete for binding, the magnetic-bead binding assay was repeated in the presence of the plectin antibody. In all cell lines tested, fewer cells bound to PCS2-magentic-beads in the presence of plectin antibody (FIG. 22B). Since previous reports have shown cells to be sufficiently stable for further assays with plectin knock-down, plectin knockdown was conducted in H358, H1693, H1975 and H1993 cells using siRNA using the magnetic-bead binding assay described above. A dramatic decrease in plectin bound cells in the plectin knockdown compared to the control siRNA treated cells was observed (FIG. 22C). From these observations, it was concluded that plectin is the cell-surface marker that PCS2 is targeting.

Figure 23A:
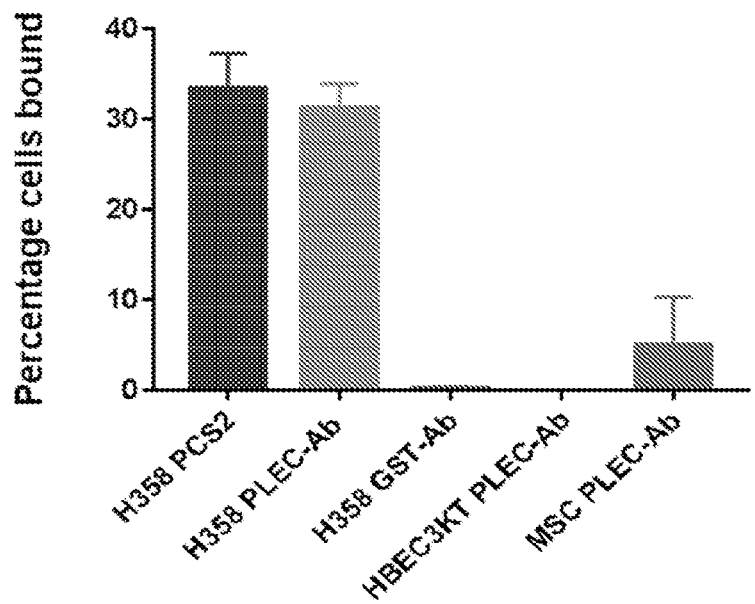
FIG. 23A is a graphical representation of the relative binding affinity of cells treated with PCS2 and plectin anti-body coated beads. Both bead types binds at similar strength indicating a same target.
Figure 23B:
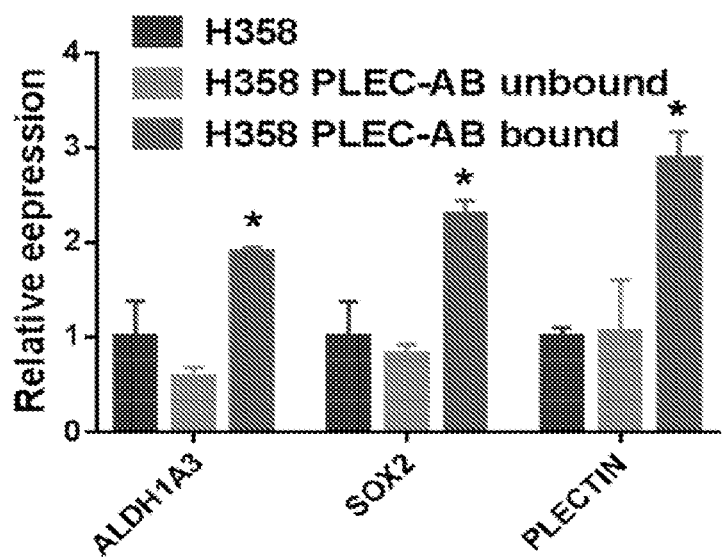
FIG. 23B is a graphical representation showing that ALDH1A3, SOX2, and PLEC expression levels were significantly higher in plectin-antibody-bound cells, than in unsorted or unbound cells
Figure 23C:
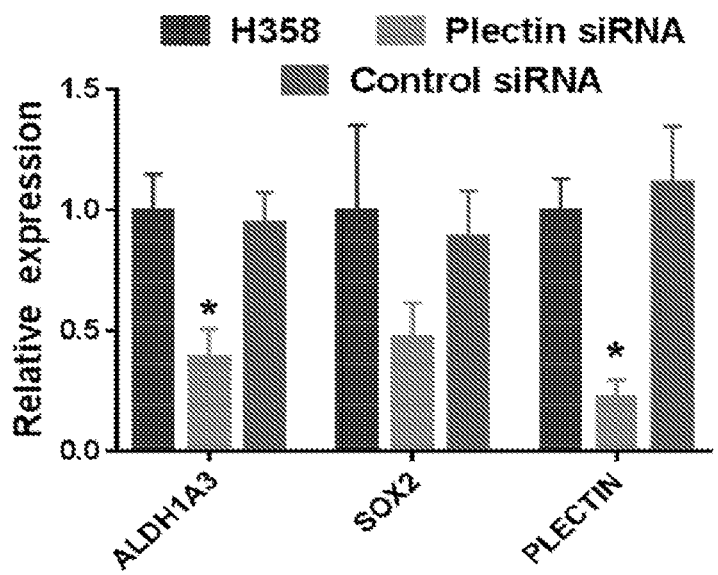
FIG. 23C is a graphical representation showing a drop in ALDH1A3, SOX2, and PLEC expression levels during a standard siRNA plectin knockdown in H358 cells.
Figure 23D:
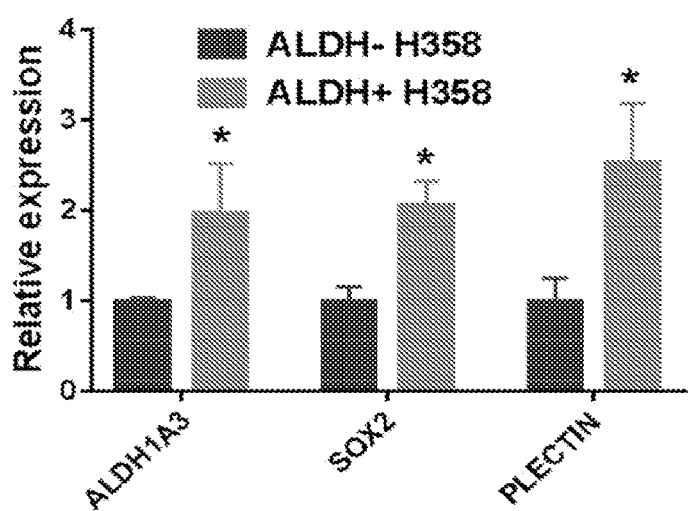
FIG. 23D is a graphical representation showing the relative expression of plectin was significantly higher in the H358 ALDH+ subpopulation than that of in the H358 ALDH− subpopulation
Figure 24:
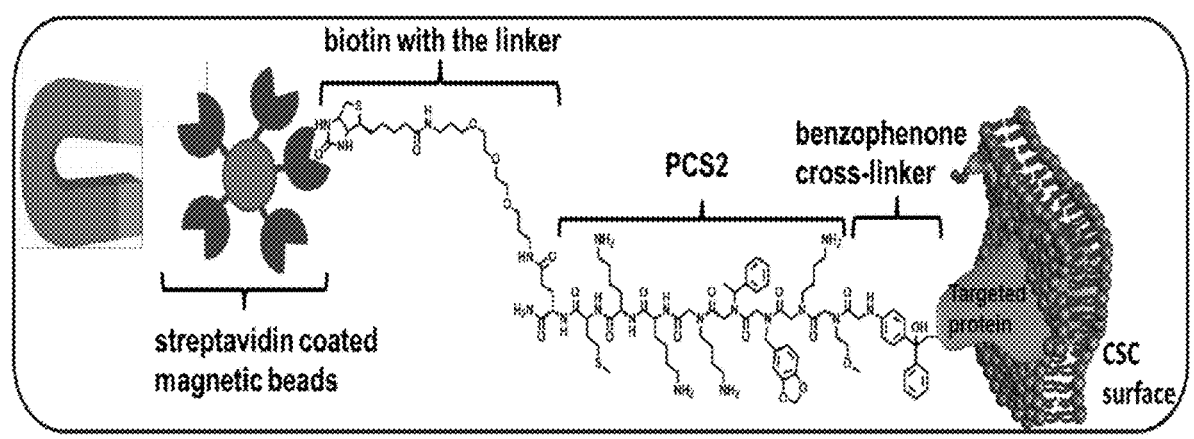
FIG. 24 is an outline of the PCS2 coated magnetic bead pull-down assay.

The initial data (FIGS. 19A, 19B, 19E) indicates that the cells isolated through PCS2-plectin based interaction express CSC biomarkers such as CD44, SOX2, CD133 and ALDH1A3 over the non-bound cells. To further evaluate this plectin-CSC connection, it was confirmed that CSCs can be isolated through cell surface plectin via a PCS2-independent approach. The same magnetic-bead pull-down assay was used as described above, but with commercially available biotinylated anti-plectin antibody instead of biotinylated-PCS2 to pull-down cells. The plectin antibody isolated approximately 28-33% of cells from H358, which is comparable to the 28-38% pull-down with PCS2 (FIG. 23A). The same anti-plectin antibody-coated magnetic beads did not pull down cells from normal HBEC3KT and MSC pull-down was minimal (FIG. 23A). This binding pattern of anti-plectin antibody towards H358, HBEC3KT and MSC is very similar to the binding pattern of PCS2 shown in FIG. 234 and FIG. 20 At the same time, anti-GST antibody coated magnetic beads could not pull down cells from H358, further confirming that this H358 cell subpopulation pull-down observation was indeed an anti-plectin antibody-specific binding event (FIG. 23A). Next the mRNA levels of two known CSC biomarkers was analyzed on these cell groups by RT-QPCR, along with plectin (PLEC). The ALDH1A3, SOX2, and PLEC expression levels were significantly higher in plectin-antibody-bound cells, than in unsorted or unbound cells (FIG. 23B), indicating the cell subpopulation pulled down from H358 carries those CSC signatures. With this observation, it was decided to test if plectin knockdown would have an effect on CSC gene expression. A standard siRNA knockdown experiment was performed and analyzed the mRNA levels of ALDH1A3, SOX2, and PLEC in H358 cells. A significant drop of all these 3 gene expression levels was observed upon the plectin knockdown on H358 cells (FIG. 23C). The control siRNA had no effect on the expression of any of these genes. As these experiments determined that plectin$^+$ cells expressed higher levels of CSC markers in H358, as assessment was conducted to determine if a CSC subpopulation had higher levels of plectin. To determine this, the expression levels of the same three genes on ALDH$^+$ and ALDH$^-$ cells that were separated using ALDEFluor assay kit as described above were tested. Plectin expression was significantly higher in the H358 ALDH+ subpopulation than that of in the H358 ALDH- subpopulation (FIG. 25D). All these observations indicate that plectin is found on the cell surface of a subpopulation of H358 cells that is ALDH+, with higher SOX2 and ALDH1A3 expression, all consistent with CSC characteristics.

Figure 25A:
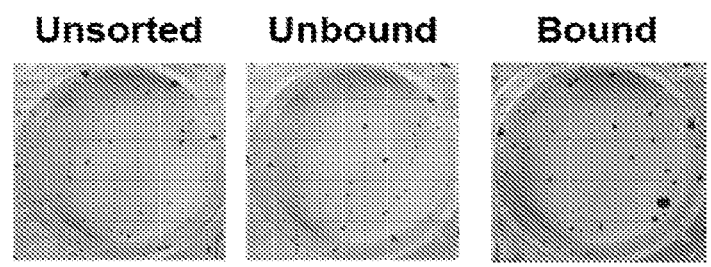
FIG. 25A is a series of photographs of plates showing the different potentials for colony formation of cells sorted by Plectin antibody-coated-magnetic beads and unsorted cells. Shown is a photograph of a plate showing the colony forming potential of unsorted cells, a photograph of a plate showing the colony forming potential of cells in the unbound fraction when sorted by Plectin antibody-coated magnetic beads, and a photograph of a plate showing the colony forming potential of cells that bound to Plectin antibody-coated magnetic beads.
Figure 25B:
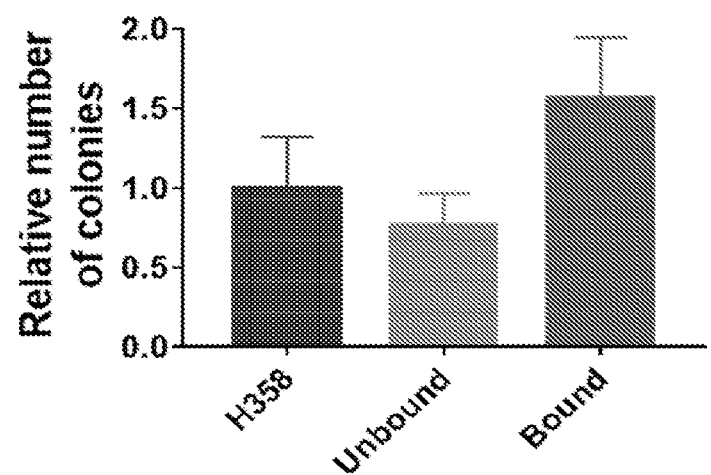
FIG. 25B is a graphical representation of the relative number of colonies for cells sorted by Plectin antibody-coated magnetic beads and unsorted cells.
Figure 25C:
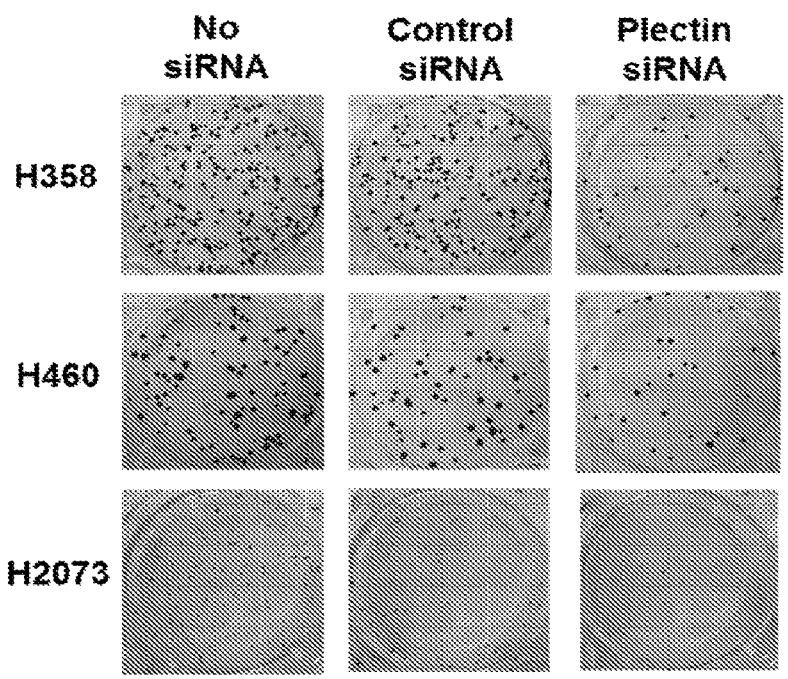
FIG. 25C is a series of photographs of plates showing the different potentials for colony formation of cells after plectin knockdown.
Figure 25D:
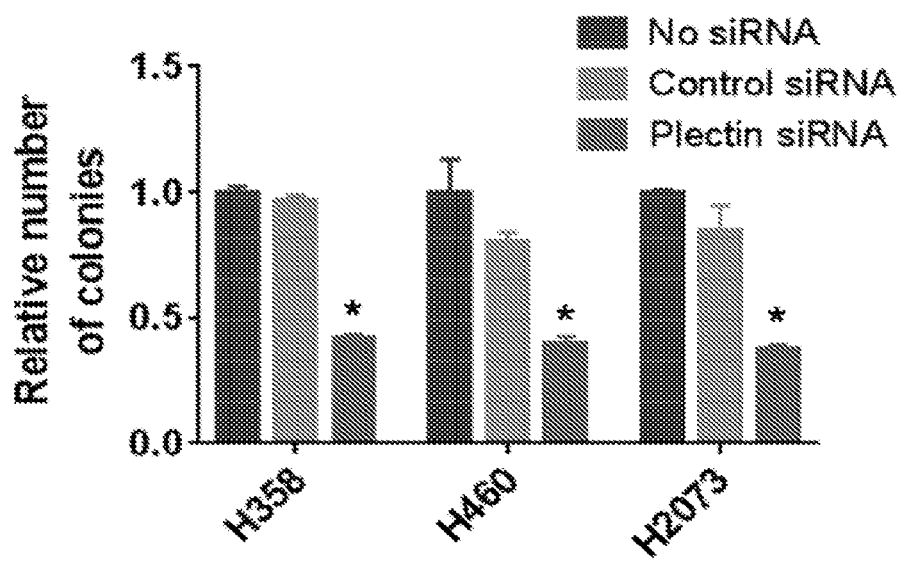
FIG. 25D is a graphical representation showing relative numbers of colonies in several cell lines after a standard siRNA knockdown.
Figure 25E:
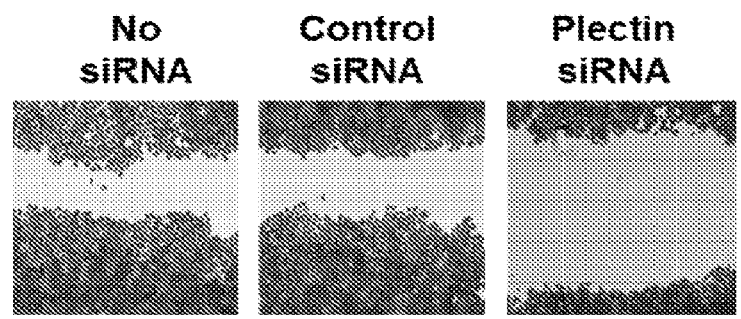
FIG. 25E is a set of photographs of the scratch assay performed on control siRNA treated and plectin knocked down H358 cells.
Figure 25F:
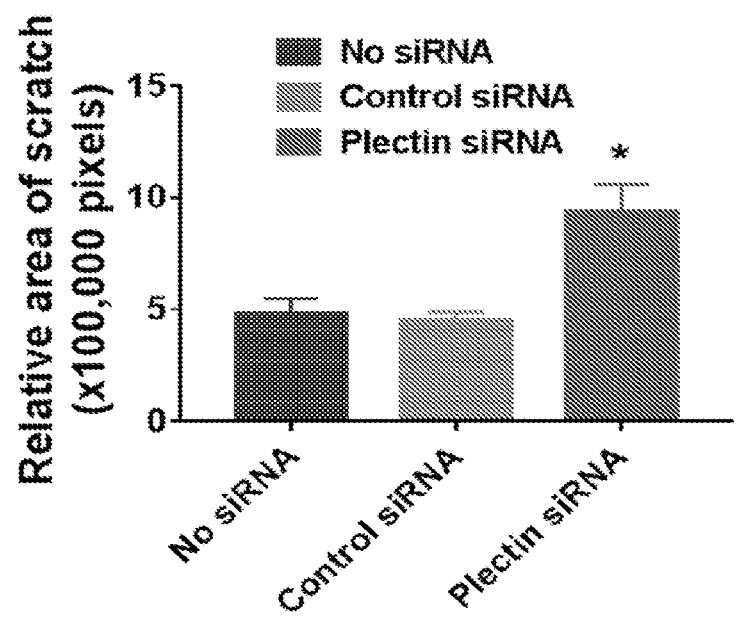
FIG. 25F is a graphical representation of the relative area of the scratch assay performed on control siRNA treated and plectin knocked down H358 cells.

To further validate these results described above, clonogenecity assays were performed using anti-plectin antibody bound, unbound and unsorted H358 cells and found the anti-plectin antibody bound cell group developed more colonies than that of unbound and unsorted H358 cells (FIGS. 25A, 25B). It was determined that the presence of plectin contributes to colony formation and wound healing potential of H358 cells. Plectin antibody-coated magnetic-bead bound fractions form a higher number of colonies compared to unbound and unseparated fraction in the clonogenicity assay in H358 cells The clonogenecity after plectin knockdown was then tested in H358, H460, and H2073 cells (FIG. 25C, 25D). Knockdown of plectin decreases colony formation in H358, H460 and H2073 cells. Knockdown of plectin leads to a decrease in mobility and scratch healing in H358 cells. The error bars shown in the figures represent standard deviation between replicates. * represents p value <0.05. Since plectin expression has previously been shown to be associated with migration and invasion in other cancer types, a "scratch" wound healing/mobility assay was performed on control siRNA treated and plectin knocked down H358 cells (FIGS. 25E, 25F). This assay has been utilized as a standard assay to test the mobility, migration and invasion potential of cancer cells. Both untreated and control siRNA treated H358 cell groups had a significantly decreased scratch width after 24 hours compared to the plectin siRNA treated cell group, indicating that plectin knockdown reduced the mobility and migration potential of H358 cells Overall, these findings indicate plectin can play a role in clonogenicity and migration/invasion of H358 NSCLC cells, which are both hallmark characteristics of CSCs.

Example 9

Further Confirmation of Functional Effect of PCS2

Figure 26:
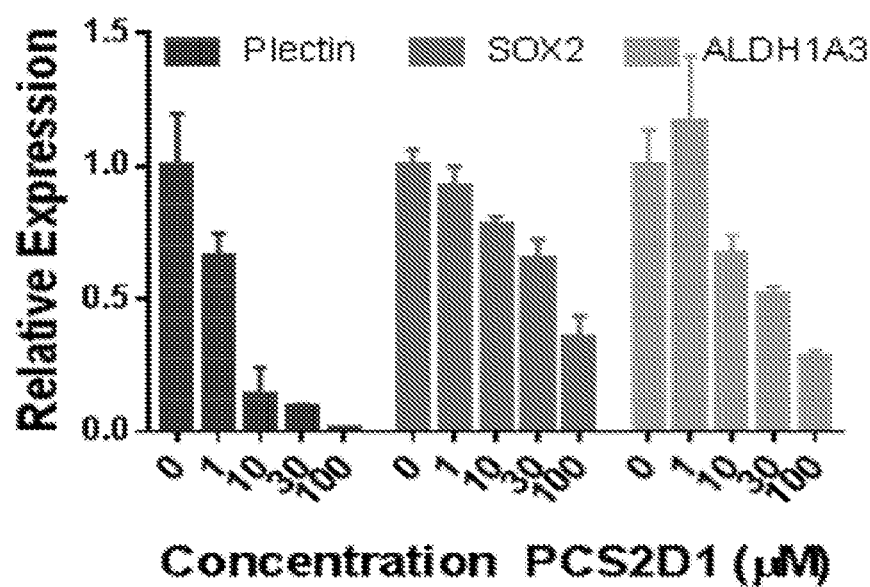
FIG. 26 is a graphical representation of the reduction of Plectin, SOX2 and ALDH1A3 upon the treatment of PCS2D1 on unsorted H358 cells, detected on the $4^{th}$ day after the treatment.

Further experiments were conducted to evaluate how impact of the compounds on the proliferation of unsorted cancer cell populations. H358 cells were treated with of 0, 0.3, 1, 3 10, 30 or 100 µM of PCS2D1 as described in Example 4. When H358 cells treated with 100 µM of PCS2D1 were tested for expression of CSC markers PLEC, ALDH1A3 and SOX2 after 96 hours of treatment, there was a significant drop in the expression of each one of those genes (FIG. 26). This confirmed that PCS2-treatment may have reduced the numbers of PLEC-, ALDH1A3- and SOX2-expressing CSCs, causing an overall decrease in cell growth.

Example 10

Dimers

Figure 5B:
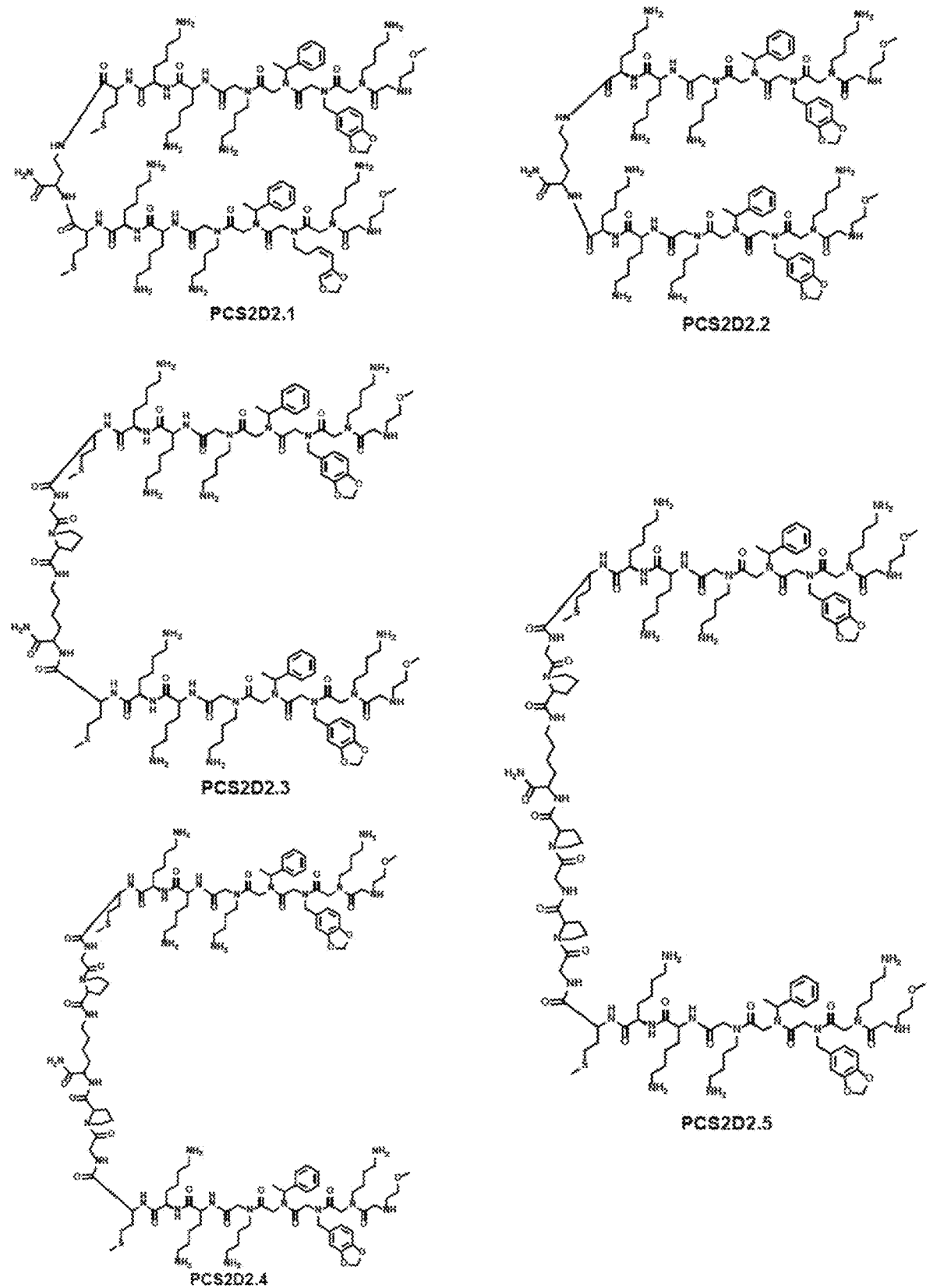
Figure 27A:
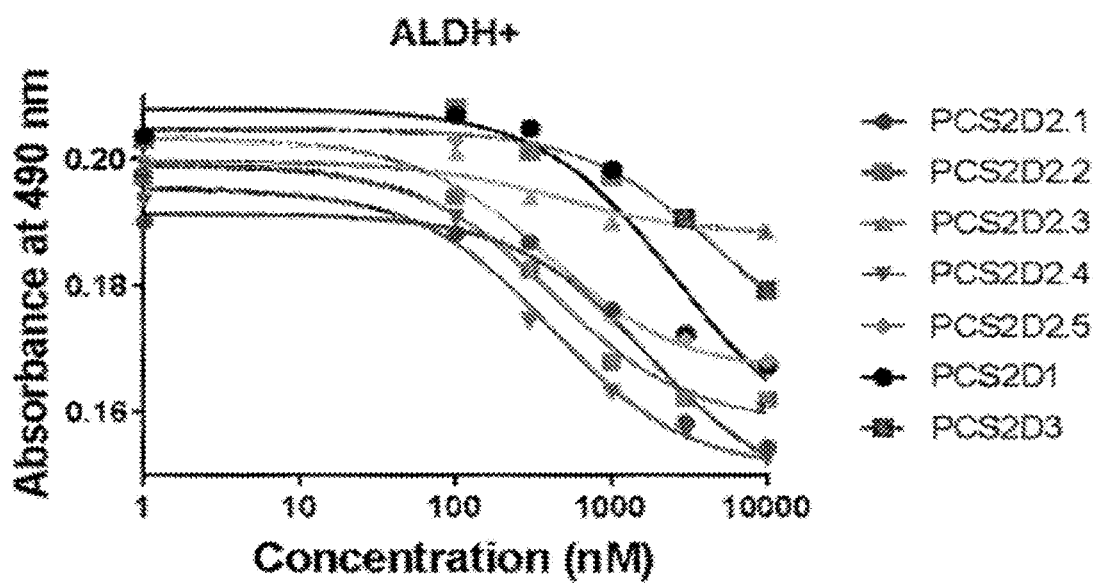
FIGS. 27A-27B are a graphical representation of MTS cytotoxic data upon the treatment of extended PCS2 dimer series compounds (shown on FIG. 5B) on H358 ALDH+ (FIG. 27A) and H358 ALDH− cells (FIG. 27B). About a 5-10 fold improvement of the cytotoxic activity is observed.
Figure 27B:
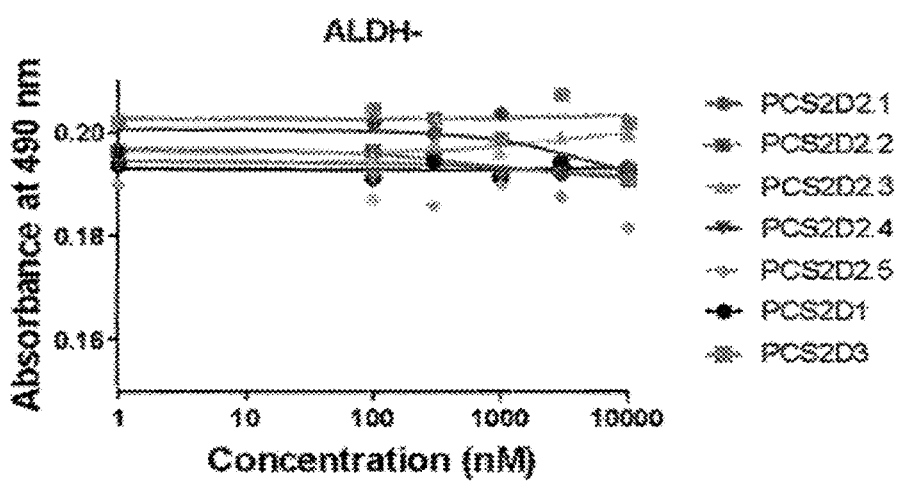

Since the PCS2D1 dimer appear to be particularly effective, a series of more dimers were synthesized with variable linker lengths and linker region rigidity as shown in FIG. 5B. All these dimers displayed improved CSC cytotoxicity when performed the MTS assay with separated H358 ALDH+ and H358 ALDH− cell groups as described in FIG. 10. All the dimers were active only on H358 ALDH+ cells (CSCs) (FIG. 27A) and no effects on H358 ALDH− cells (remaining cancer cells) (FIG. 27B). There were 5-10 fold-improvements observed, with IC50 values at mid-nano molar range (around 200 nM). These improved derivatives are currently under investigations on other assays.

Those skilled in the art will recognize, or be able to ascertain using no more than routine experimentation, many equivalents to the specific embodiments of the invention described herein. Such equivalents are intended to be encompassed by the following claims.

The invention claimed is:

1. A pharmaceutical composition comprising a peptoid compound having the General formula (II), an isomer thereof, or a pharmaceutically acceptable derivative thereof:

General formula (II)

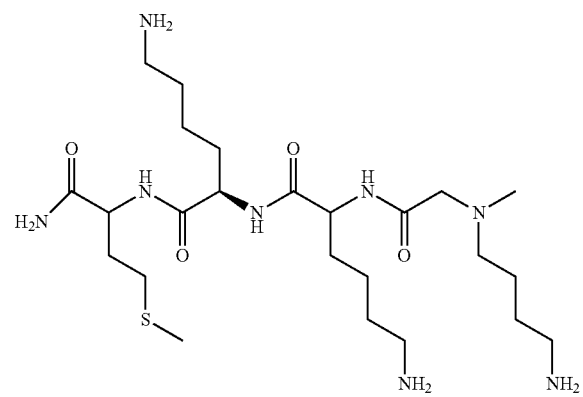

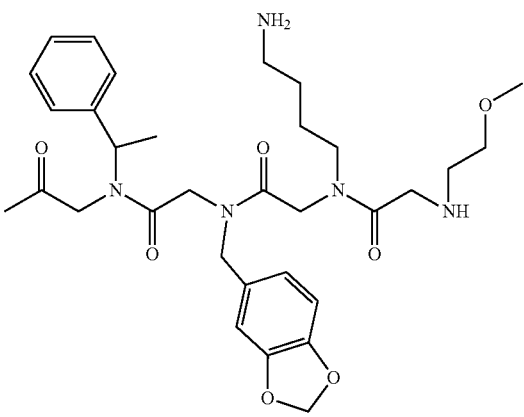

2. The pharmaceutical composition of claim 1, wherein the peptoid compound is present in a therapeutically effective amount in the pharmaceutical composition.

3. A method for reducing proliferation of a cancer stem cell in a subject, the method comprising administering to the subject the pharmaceutical composition of claim 1.

4. The method of claim 3, wherein said cancer stem cell is a leukemia cancer stem cell.

5. The method of claim 3, wherein the cancer stem cell is present as part of a cancerous cell mass.

6. The method of claim 5, wherein cancerous cell mass contains a cell selected from the group consisting of a glioblastoma cell, a melanoma cell, a colon cancer cell, a prostate cancer cell, a lung cancer cell, a pancreatic cancer cell, a hepatic cancer cell, an ovarian cancer cell, and a breast cancer cell.

7. A method for detecting presence of a cancer stem cell in a human tissue sample, the method comprising contacting the human tissue with a peptoid compound having General formula (II):

General formula (II)

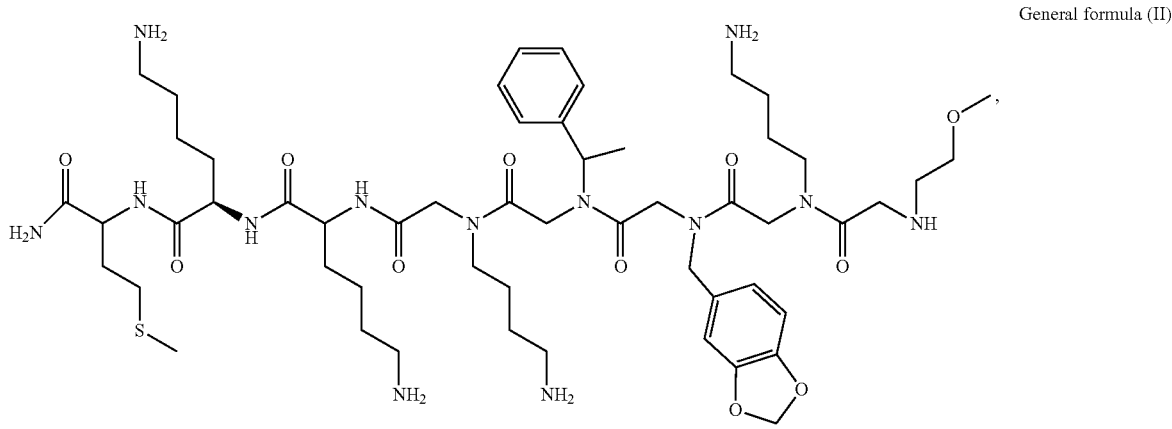

and detecting binding of said peptoid compound with the cancer stem cell.

8. The method of claim 7, wherein binding is mediated by plectin present in the cancer stem cell.

9. The method of claim 7, wherein said cancer stem cell is a leukemia cancer stem cell.

10. The method of claim 7, wherein the cancer stem cell is present as part of a cancerous cell mass.

11. The method of claim 10, wherein cancerous cell mass contains a cell selected from the group consisting of a glioblastoma cell, a melanoma cell, a colon cancer cell, a prostate cancer cell, a lung cancer cell, a pancreatic cancer cell, a hepatic cancer cell, an ovarian cancer cell, and a breast cancer cell.

* * * * *